United States Patent
Nagai et al.

(10) Patent No.: US 7,983,730 B2
(45) Date of Patent: Jul. 19, 2011

(54) METHOD FOR ACQUIRING RESPIRATORY DISEASE-RELATED ANALYSIS DATA, OXIMETER SYSTEM, OPERATION PROGRAM PRODUCT FOR OXIMETER SYSTEM, OXIMETER, AND OXYGEN SUPPLY SYSTEM

(75) Inventors: Yoshiroh Nagai, Nishinomiya (JP); Kazumi Kitajima, Higashiosaka (JP)

(73) Assignee: Konica Minolta Sensing, Inc., Sakai-shi (JP)

( * ) Notice: Subject to any disclaimer, the term of this patent is extended or adjusted under 35 U.S.C. 154(b) by 1530 days.

(21) Appl. No.: 11/367,623

(22) Filed: Mar. 3, 2006

(65) Prior Publication Data
US 2006/0217603 A1 Sep. 28, 2006

(30) Foreign Application Priority Data
Mar. 23, 2005 (JP) ................... 2005-083712

(51) Int. Cl.
*A61B 5/00* (2006.01)
*F16K 31/02* (2006.01)
(52) U.S. Cl. ................... 600/324; 128/204.23
(58) Field of Classification Search ............... None
See application file for complete search history.

(56) References Cited

U.S. PATENT DOCUMENTS

| | | | |
|---|---|---|---|
| 6,120,441 A * | 9/2000 | Griebel | 600/300 |
| 6,322,515 B1 | 11/2001 | Goor et al. | |
| 7,668,579 B2 * | 2/2010 | Lynn | 600/323 |
| 2005/0288729 A1 * | 12/2005 | Libbus et al. | 607/42 |
| 2006/0149144 A1 * | 7/2006 | Lynn et al. | 600/323 |
| 2006/0155206 A1 * | 7/2006 | Lynn | 600/529 |
| 2006/0235324 A1 * | 10/2006 | Lynn | 600/538 |
| 2007/0129647 A1 * | 6/2007 | Lynn | 600/538 |
| 2007/0191688 A1 * | 8/2007 | Lynn | 600/300 |
| 2007/0191697 A1 * | 8/2007 | Lynn et al. | 600/323 |
| 2010/0174161 A1 * | 7/2010 | Lynn | 600/323 |
| 2010/0234705 A1 * | 9/2010 | Lynn | 600/324 |

FOREIGN PATENT DOCUMENTS

JP 2000-5145 A 1/2000

OTHER PUBLICATIONS

Japanese Notice of Reasons for Rejection dated Jul. 27, 2010, for counterpart Japanese Application No. 2005-083712, together with an English translation thereof.

* cited by examiner

*Primary Examiner* — Long V Le
*Assistant Examiner* — Angela M Hoffa
(74) *Attorney, Agent, or Firm* — Sidley Austin LLP

(57) ABSTRACT

An oximeter system includes a blood oxygen saturation detector for detecting blood oxygen saturation information of a subject, a body motion detector for detecting body motion information of the subject, a controller for causing the blood oxygen saturation detector to acquire the blood oxygen saturation information, and causing the body motion detector to acquire the body motion information at a predetermined sampling frequency concurrently and respectively sequentially, and a display unit for displaying data concerning the acquired blood oxygen saturation information and data concerning the acquired body motion information along a common time axis.

9 Claims, 31 Drawing Sheets

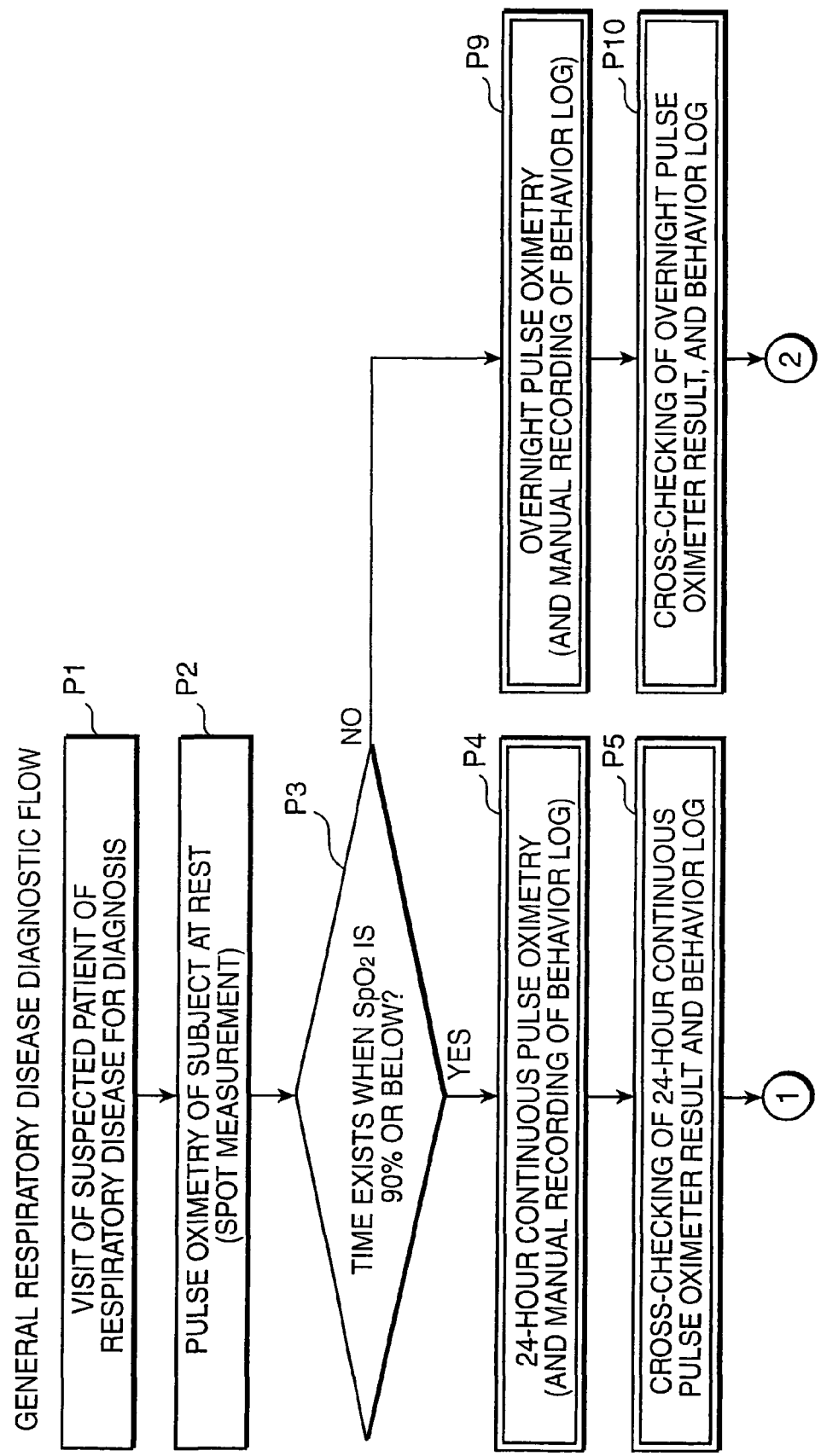

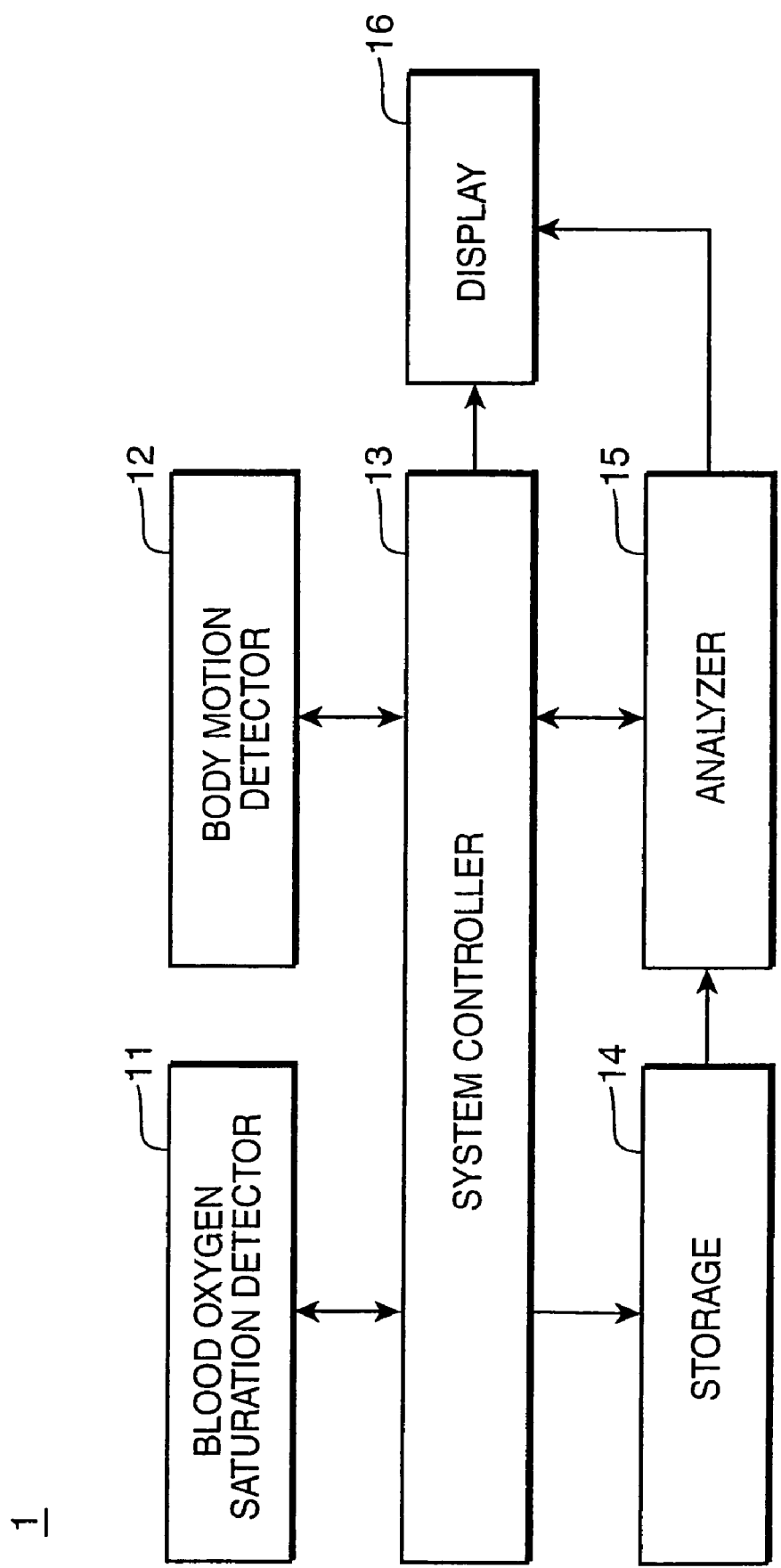

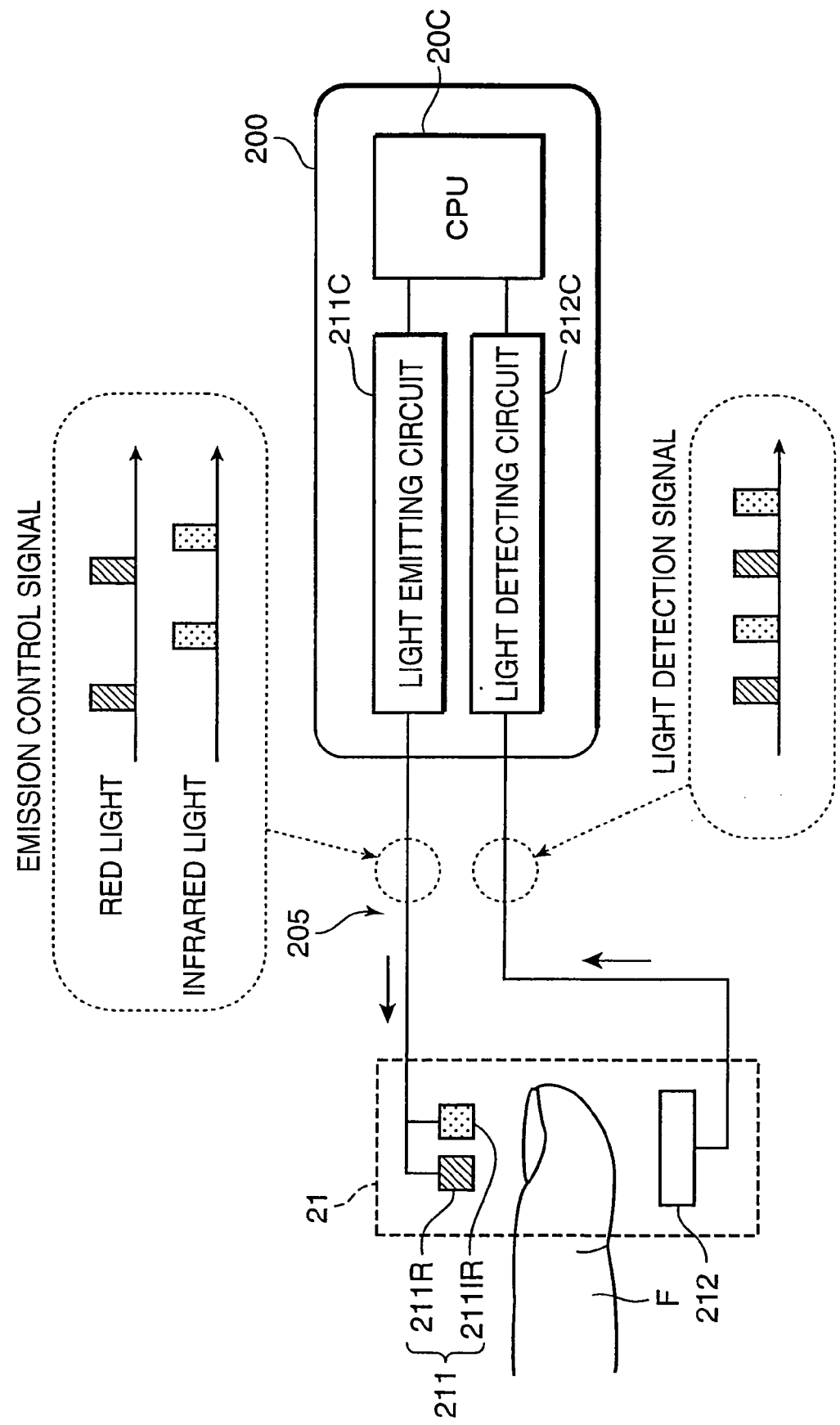

FIG.21

| EXERCISE AMOUNT | LOWEST SpO₂ (%) | | | | | | |
|---|---|---|---|---|---|---|---|
| | 84 | 85 | 86 | 87 | 88 | 89 | 90 |
| 1000 | 2.1 | 2.0 | 1.9 | 1.8 | 1.7 | 1.6 | 1.6 |
| 2000 | 2.0 | 1.9 | 1.8 | 1.7 | 1.6 | 1.5 | 1.4 |
| 3000 | 1.9 | 1.8 | 1.7 | 1.6 | 1.5 | 1.4 | 1.3 |
| 4000 | 1.8 | 1.7 | 1.6 | 1.5 | 1.4 | 1.3 | 1.2 |
| 5000 | 1.7 | 1.6 | 1.5 | 1.4 | 1.3 | 1.2 | 1.1 |
| 6000 | 1.6 | 1.5 | 1.4 | 1.3 | 1.2 | 1.1 | 1.0 |

METHOD FOR ACQUIRING RESPIRATORY DISEASE-RELATED ANALYSIS DATA, OXIMETER SYSTEM, OPERATION PROGRAM PRODUCT FOR OXIMETER SYSTEM, OXIMETER, AND OXYGEN SUPPLY SYSTEM

This application is based on Japanese Patent Application No. 2005-83712 filed on Mar. 23, 2005, the contents of which are hereby incorporated by reference.

BACKGROUND OF THE INVENTION

1. Field of the Invention

The present invention relates to an oximeter system designed so that a correlation between body motion and occurrence of respiratory failure can be recognized accurately for a patient or a suspected patient having a respiratory disease such as chronic respiratory failure or quasi chronic respiratory failure.

2. Description of the Related Art

In diagnosing a patient having a respiratory disease, it is essential to accurately recognize a causal relation or a correlation between body motion and respiratory disease presentation of the patient to determine a suitable therapeutic measure such as selection of a therapeutic apparatus or prescription of an oxygen flow rate. Specifically, therapeutic measures are different among the patients depending on conditions as to whether a respiratory disease is presented at the time of an exercise while the patient is awake, the amount of exercise, i.e., the degree of exercise which may cause the respiratory disease, whether the respiratory disease is presented even while the patient is at rest, whether the respiratory disease is presented mainly while the patient is in sleep, or other condition. There is an approach of measuring a variation in oxygen saturation in an arterial blood (hereinafter, called as "blood oxygen saturation" or "SpO$_2$") of a subject including a patient, as an approach of recognizing a condition of the subject having a respiratory disease. This approach is proposed utilizing a phenomenon that a respiratory failure induces blockage of oxygen supply, which resultantly lowers the blood oxygen saturation.

Conventionally, as shown in FIG. 30, for instance, there has been an approach, in which the blood oxygen saturation of a subject is serially measured by attaching a pulse oximeter to the subject, and a daily behavior log of the subject which has been manually recorded by the subject or a nurse, and the time-based change of the blood oxygen saturation are cross-checked to recognize a correlation between body motion and presentation of a respiratory disease. FIG. 30 is a time chart, in which behavior events are logged on a measurement result of a continuous pulse oximetry. A judgment is made as to whether the blood oxygen saturation is lowered in association with the body motion of the subject based on the measurement data. If there is found a correlation between body motion and respiratory failure of the subject, use of home oxygen therapy (HOT) is considered, or an oxygen flow rate is prescribed. If there is not found a correlation between body motion and respiratory failure of the subject, use of nasal intermittent positive pressure ventilation (NIPPV) is considered.

There is known a system for concurrently measuring the blood oxygen saturation of a subject, and detecting a body motion of the subject. The system noninvasively confirms endothelial dysfunction, breathing disorder due to hypopnea during sleep, or upper airway resistance syndrome (UARS), as well as biophysical state of a subject regarding activity or reactivity of autonomic nervous system, or responsiveness to pharmacological agent. The system is provided with an actigraph for judging whether a subject is in sleep or awake, and a pulse oximeter for measuring a blood oxygen saturation of the subject to diagnose sleep apnea syndrome (SAS).

In diagnosing the disease based on the measurement data as shown in FIG. 30, a subject or a nurse is required to manually record a behavior log of the subject at the time when the blood oxygen saturation is measured by a pulse oximeter, which increases a labor involved in collecting the data. Also, it takes a certain time and labor in combining the measurement result by the pulse oximeter and the behavior log. Further, there is a case that it is difficult to judge whether lowering of the blood oxygen saturation is due to body motion because the recorded time of an event is uncertain, or an event has not been logged. The lowering degree of the blood oxygen saturation is normally varied due to a degree of body motion, an exercise time, or an exercise amount. Since the daily behavior is logged manually, it is difficult to objectively judge the exercise amount, which takes a time in prescribing an optimal oxygen flow rate.

The conventional arrangement discloses combination of an actigraph and a pulse oximeter as a sleep diagnostic system. However, the arrangement does recite or suggest application of the system to treating subjects of chronic respiratory failure or quasi chronic respiratory failure. This means that there has not been found a diagnostic approach regarding chronic respiratory failure and quasi chronic respiratory failure by correlating a measurement result of a pulse oximeter to a measurement result of an actigraph. In other words, there has not been found an approach of acquiring analysis data beneficial to a subject by linking a measurement result of an actigraph to a measurement result on blood oxygen saturation of a pulse oximeter.

SUMMARY OF THE INVENTION

It is an object of the present invention to provide a new body condition measurement technology which has overcome the problems residing in the prior art.

It is another object of the present invention to provide a pulse oximeter system that enables to easily and accurately acquire a correlation between body motion and respiratory disease presentation of a subject as objective analysis data without the need of manually recording a behavior log.

According to an aspect of the present invention, analysis data concerning a respiratory disease is acquired by detecting a blood oxygen saturation and a body motion of a subject at a predetermined sampling frequency concurrently and respectively sequentially, expressing data concerning the detected blood oxygen saturation and data concerning the detected body motion along a common time axis, and acquiring analysis data concerning a relation between a change in the blood oxygen saturation and the body motion of the subject based on the blood oxygen saturation data and the body motion data expressed along the common time axis.

These and other objects, features and advantages of the present invention will become more apparent upon reading of the following detailed description along with the accompanying drawings.

BRIEF DESCRIPTION OF THE DRAWINGS

FIGS. 1A and 1B are flowcharts showing a general flow of diagnosing a respiratory disease.

FIG. 2 is a block diagram schematically showing an entire arrangement of an oximeter system in accordance with an embodiment of the invention.

FIG. 5 is a circuit diagram schematically showing a circuit configuration of the pulse oximeter.

FIGS. 6A through 6C are illustrations showing a three-axis acceleration sensor using a piezoresistor, as an example of a three-axis acceleration sensor, wherein FIG. 6A is a perspective view of the three-axis acceleration sensor, FIG. 6B is a top plan view thereof, and FIG. 6C is a cross-sectional view taken along the line 6C-6C in FIG. 6B.

FIG. 21 is an illustration showing an example of an oxygen flow rate table showing a correlation between lowest $SpO_2$ value and exercise amount peak value.

DETAILED DESCRIPTION OF THE PREFERRED EMBODIMENTS OF THE INVENTION (Description on General Flow of Diagnosing Respiratory Disease)

Figure 1B:
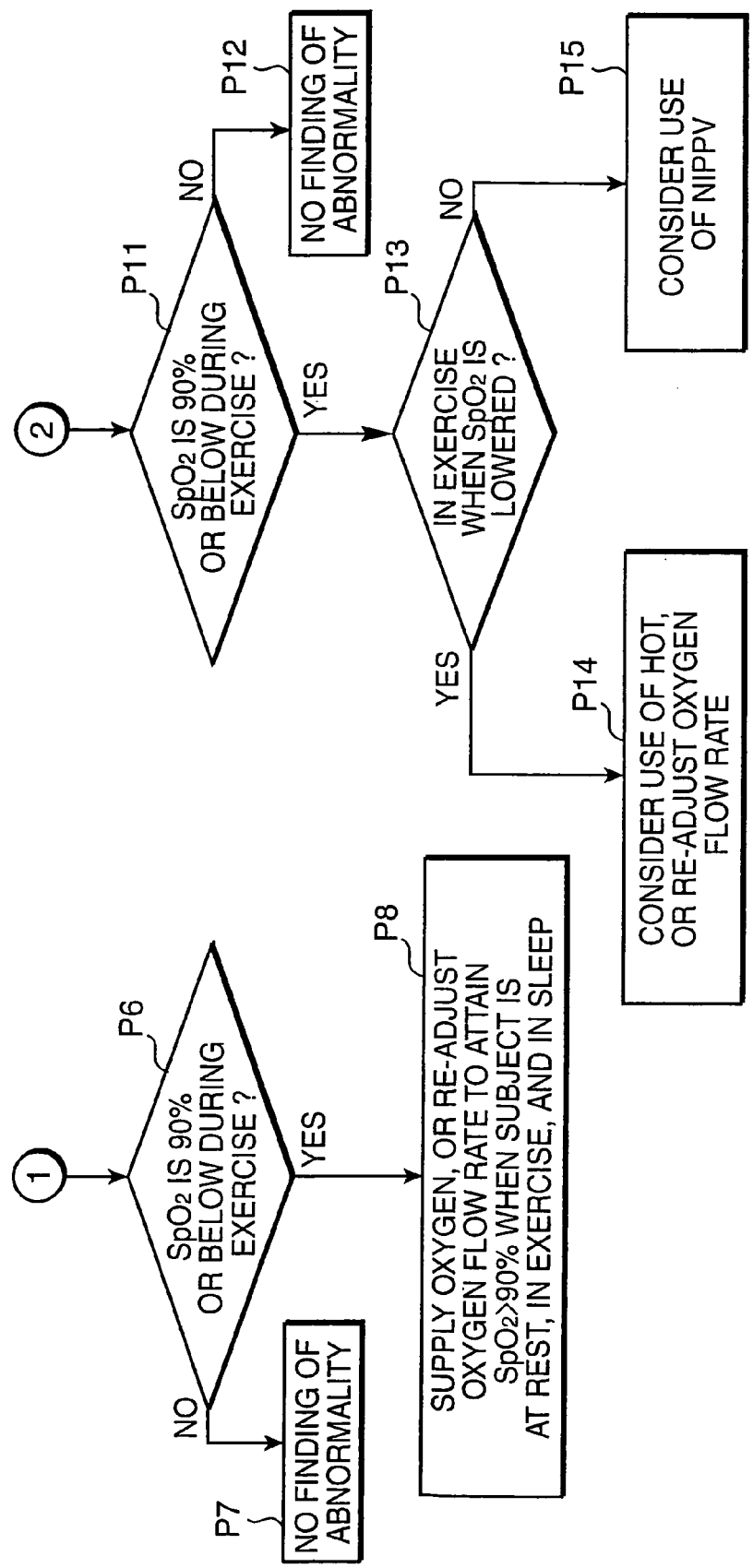

Before describing an oximeter system according to an embodiment of the invention, a current system of diagnosing a respiratory disease with use of an oximeter system is described referring to a flow. FIGS. 1A and 1B are flowcharts showing a general flow in diagnosing a respiratory disease of a subject. In the diagnostic system, it is confirmed whether aftereffect of pulmonary tuberculosis (TB), or a respiratory disease such as chronic respiratory failure or quasi chronic respiratory failure resulting from pneumonectasia is presented, or a symptom is mainly presented while the subject is in sleep, or a correlation is found between body motion and respiratory failure of the subject. As a therapeutic approach, a judgment is made whether home oxygen therapy (HOT), in which the subject is put on oxygen at home for a long term is conducted, or a non-invasive intermittent positive pressure ventilation (NIPPV) is conducted. Also, the oxygen flow rate in the therapeutic approach is determined. If sufficient night-time carbon dioxide gas exhaustion is not performed in the patients who received treatment of the HOT, use of the NIPPV is considered.

Referring to FIGS. 1A and 1B, when a subject, namely, a suspected patient of a respiratory disease visits a clinic for diagnosis (Step P1), a pulse oximeter is attached to the subject, and a spot pulse oximetry is started while the subject is at rest (Step P2). At the spot oximetry, it is judged whether there exists a time when the blood oxygen saturation ($SpO_2$) falls 90% or below, which is a criteria for appearance of hypoxemia (Step P3). Step P3 is conducted to judge whether it is necessary to execute 24-hour continuous pulse oximetry or overnight pulse oximetry.

Figure 30:
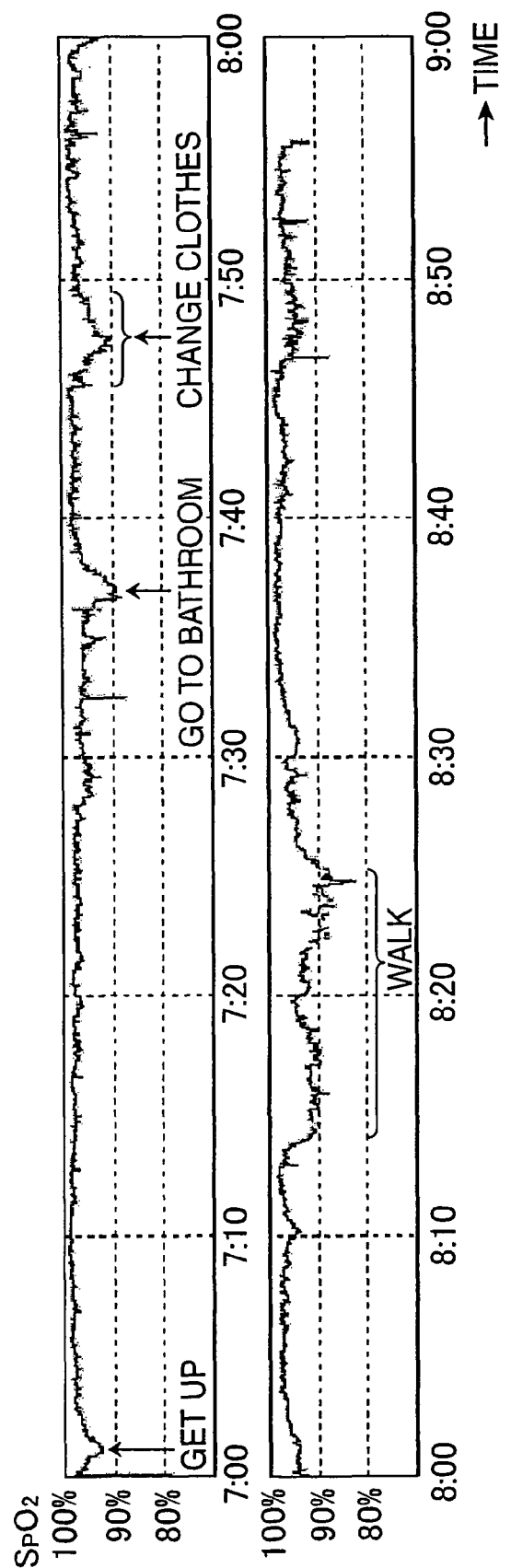
FIG. 30 is an illustration showing an approach of detecting a correlation between body motion and respiratory disease presentation according to the conventional art.

If there is observed a time when the $SpO_2$ falls 90% or below in the subject (YES in Step P3), 24-hour continuous pulse oximetry is conducted for the subject to examine a relation between body motion or exercise, and lowering of $SpO_2$ over night and day (Step P4). A time-based change of the $SpO_2$ is measured by the pulse oximeter, and a daily behavior log indicating exercise information is manually recorded by the subject and/or a nurse. A measurement result of the 24-hour continuous pulse oximetry, namely, a time-based change of the $SpO_2$, and the behavior log of the subject are cross-checked (Step P5). The cross-checking is performed by manpower. As a result of the cross-checking, evaluation data as shown in FIG. 30 is created. In other words, manpower is necessary in Steps P4 and P5.

Subsequently, it is judged whether the $SpO_2$ falls 90% or below during the exercise based on the evaluation data (Step P6). If the $SpO_2$ does not fall below 90% (NO in Step P6), the diagnosis shows that there is no finding of abnormality (Step P7). On the other hand, if the $SpO_2$ falls 90% or below during the exercise (YES in Step P7), an oxygen flow rate is prescribed or re-adjusted to constantly attain $SpO_2 > 90\%$ while the subject is at rest, in exercise, and in sleep (Step P8).

If the judgment result in Step P3 is negative, overnight pulse oximetry is conducted to confirm an overnight respiratory failure state of the subject (Step P9). At this time, the behavior of the subject is manually logged by a nurse or an equivalent person. Then, the measurement result of the overnight pulse oximetry, namely, the time-based change of $SpO_2$, and the behavior log of the subject are cross-checked (Step P10). Manpower is also necessary in Steps P9 and P10.

After the cross-checking, it is judged whether there exists a time when the $SpO_2$ falls 90% or below (Step P11). If it is judged that no lowering of the $SpO_2$ is found (NO in Step P11), the diagnosis shows that there is no finding of abnormality (Step P12). If, on the other hand, the $SpO_2$ falls 90% or below (YES in Step P11), a relation between exercise and lowering of $SpO_2$ is confirmed based on the data created in Step P10 (Step P13). If it is judged that the $SpO_2$ is lowered during the exercise (YES in Step P13), use of the HOT is considered, or the oxygen flow rate is re-adjusted (Step P14). On the other hand, if it is judged that the $SpO_2$ is not lowered during the exercise (NO in Step P13), the subject is suspected to have a respiratory failure (type II), and accordingly, use of the NIPPV is considered (Step P15).

In this embodiment, described is an oximeter system which does not require manpower at least in Steps P4, and P5, and in Steps P9 and P10 in the respiratory disease diagnostic flow. Also, described is an oximeter system that enables to provide useful judgment data in the judgment steps P6, P11, and P13, and in the treatment steps P8 and P14. In the following, the embodiment is described in detail referring to the drawings.

(Description on Hardware Construction)

FIG. 2 is a block diagram schematically showing an entire arrangement of an oximeter system 1 as the embodiment of the invention. The oximeter system 1 is adapted to measure a blood oxygen saturation and a body motion of a subject having a respiratory disease at a predetermined sampling frequency concurrently and respectively sequentially, to express measurement data concerning the blood oxygen saturation and measurement data concerning the body motion along a common time axis, and to acquire analysis data concerning a correlation between a change in the blood oxygen saturation and the body motion of the subject. The oximeter system 1 includes a blood oxygen saturation detector 11, a body motion detector 12, a system controller 13, a storage 14, an analyzer 15, and a display unit 16.

The blood oxygen saturation detector 11 detects information relating to a blood oxygen saturation of a subject which has a close relation to presentation of respiratory failure of the subject. An example of the blood oxygen saturation detector 11 is a pulse oximeter capable of measuring the blood oxygen saturation of the subject easily by attaching a probe to a finger tip of the subject.

The body motion detector 12 detects information relating to a body motion of the subject. The body motion information is, for instance, an electrical signal to be generated in association with the body motion of the subject. An example of the body motion detector 12 is an acceleration sensor, which is mounted on a body trunk portion or an appropriate site of the subject, for generating an electrical output in association with the body motion of the subject.

The system controller 13 includes a microprocessor, and causes the blood oxygen saturation detector 11 and the body motion detector 12 to concurrently and respectively sequentially detect the blood oxygen saturation information and the body motion information of the subject at the predetermined sampling frequency, and causes the storage 14 to store the measurement data acquired by the detection operations of the blood oxygen saturation detector 11 and the body motion detector 12 therein.

The storage 14 stores the measurement data acquired by the blood oxygen saturation detector 11 and the body motion detector 12 therein, and includes a random access memory (RAM), or an erasable and programmable read only memory (EEPROM).

The analyzer 15 analyzes a relation between the change in the blood oxygen saturation and the body motion of the subject based on the measurement data concerning the blood oxygen saturation information and the body motion information, which are stored in the storage 14, and generates analysis data concerning a relation between respiratory disease presentation and body motion of the subject. For instance, the analyzer 15 generates certain analysis data representing a correlation between a body motion and a lowest peak of the blood oxygen saturation by processing the body motion information into objective data such as an exercise amount, an exercise time, or a like parameter. The display unit 16 includes a display device such as a liquid crystal display (LCD) device or a cathode ray tube (CRT) display device, and displays the analysis result by the analyzer 15 as proper image information.

The hardware construction of the oximeter system 1 may be arbitrarily designed. The following are some of the examples of the hardware construction of the oximeter system 1.

(a) Solely the sensing devices, i.e., the blood oxygen detector 11 and the body motion detector 12 are detachably attached to the subject. A personal computer (hereinafter, called as "PC") is constituted of the system controller 13, the storage 14, the analyzer 15, and the display unit 16. The PC and the sensing devices are connected by a communication line.

(b) A pulse oximeter, which serves as the blood oxygen detector 11 and is adapted to measure the blood oxygen saturation, is equipped with the body motion detector 12, the system controller 13, and the storage 14. The pulse oximeter equipped with these devices is connected to a PC serving as the analyzer 15 by a USB cable or a like device.

(c) A one-piece system is constructed by additionally providing a function of the analyzer 15 to the pulse oximeter having the arrangement (b).

Figure 3:
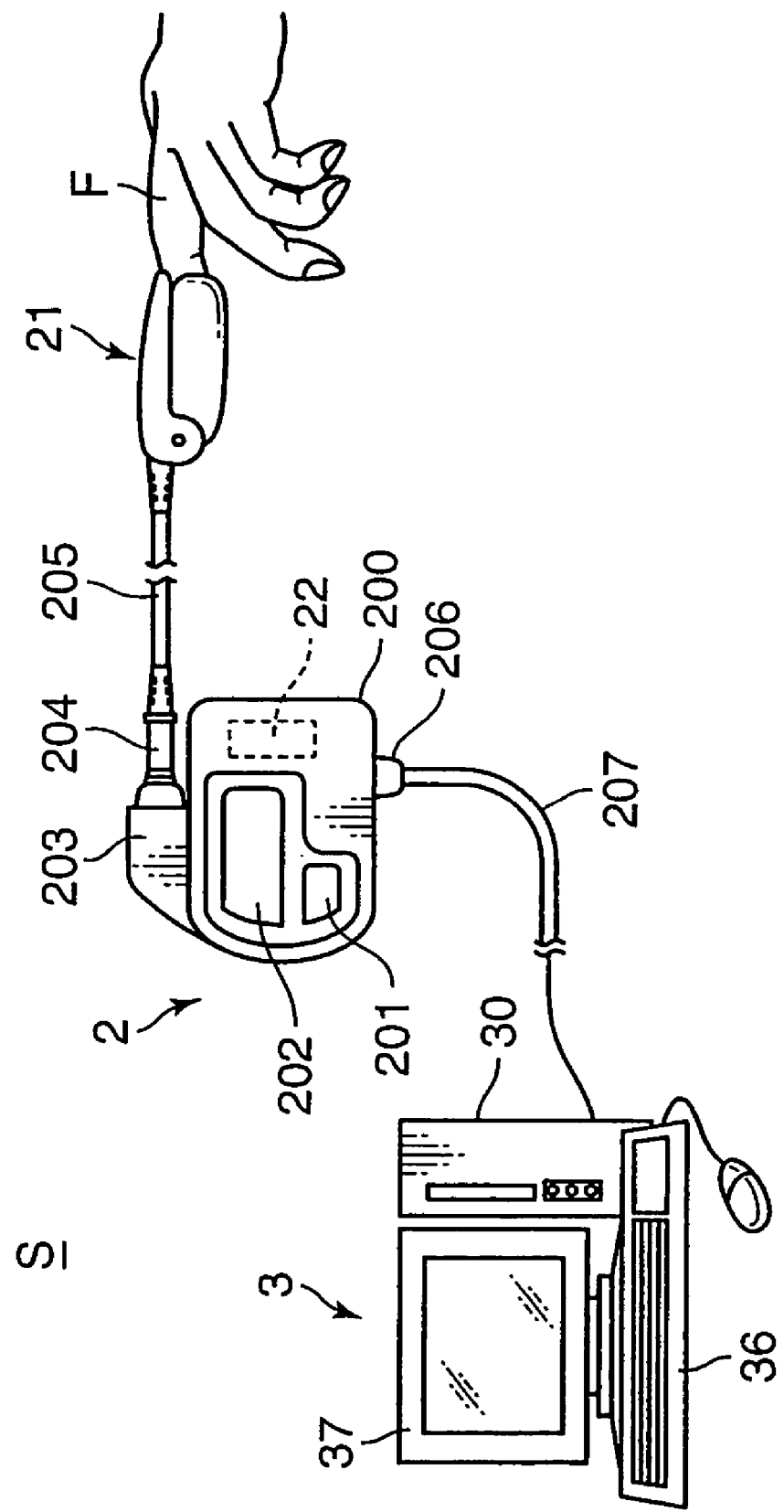
FIG. 3 is an illustration showing an example of an oximeter system having a certain hardware construction.

FIG. 3 is an illustration showing an example of an oximeter system S having the hardware construction (b). The oximeter system S includes a pulse oximeter 2 for concurrently and respectively sequentially detecting blood oxygen saturation information and body motion information of the subject at a predetermined sampling frequency to store the measurement data concerning the blood oxygen saturation information and the body motion information therein, a PC 3 for analyzing a relation between the change in the blood oxygen saturation and the body motion of the subject by reading out the measurement data stored in the pulse oximeter 2, and a USB cable 207 for communicatively connecting the pulse oximeter 2 and the PC3 according to needs.

The pulse oximeter 2 has a main body 200 and a probe 21. The oximeter main body 200 and the probe 21 are electrically connected by a probe cable 205 equipped with a connector 204. The oximeter main body 200 is externally provided with a power switch 201, an oximeter display 202 with a liquid crystal display device, a connecting portion 203 for connecting the oximeter main body 200 to the probe cable 205, and a connecting portion 206 for connecting the oximeter main body 200 to the USB cable 207. The oximeter main body 200 internally has a microprocessor, i.e., a central processing unit (CPU) serving as the system controller 13, a memory serving as the storage 14, a power battery, and a three-axis acceleration sensor 22 serving as the body motion detector 12. The memory, the microprocessor, and the power battery are not shown in FIG. 3.

The probe 21 has a paper-clip like shape capable of securely holding a finger F of a subject to measure the blood oxygen saturation of the subject. Specifically, the probe 21 has a pair of holding pieces which are openably jointed to each other so that the probe 21 can securely hold the finger F with a biasing force of a spring or a like member. As will be described later, a light emitter 211 is provided on one of the holding pieces, and a light detector 212 is provided on the other thereof (see FIG. 5).

Figure 4:
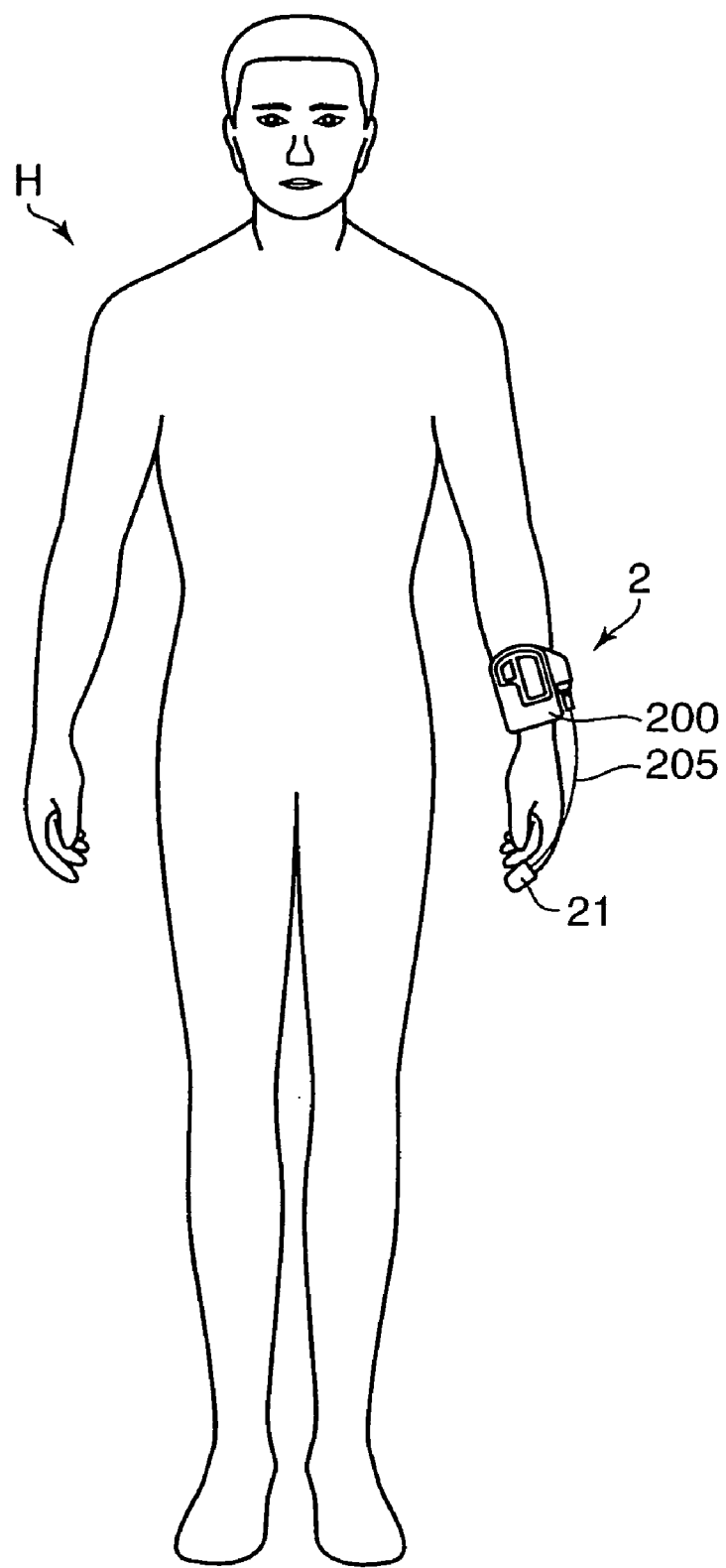
FIG. 4 is an illustration showing a mounted state of a pulse oximeter on a subject.

The oximeter main body 200 and the probe 21 are detachably attached to a subject H in the manner as shown in FIG. 4, for instance, in measurement. Specifically, a fastening belt (not shown) is wound around an arm portion of the subject H so that the oximeter main body 200 is fixed to the arm portion of the subject H with use of the fastening belt. Also, the probe 21 is fixedly attached to the finger F of the subject H for measurement. Thereafter, the oximeter main body 200 and the probe 21 are connected to each other by way of the probe cable 205. At the time of measurement, i.e., during sleep of the subject H, the USB cable 207 is not connected to the oximeter main body 200. The USB cable 207 is connected to the PC 3 after the measurement is completed to read out the measurement data from the pulse oximeter 2.

The PC 3 includes a PC main body 30, i.e., a hard disk device serving as the analyzer 15, an operating unit 36 having a keyboard and the like, and a display unit 37 having a cathode ray tube (CRT) display device or a liquid crystal display (LCD) device.

FIG. 5 is an illustration schematically showing a circuit configuration of the probe 21 and the oximeter main body 200 connected thereto. The probe 21 includes the light emitter 211 and the light detector 212. The light emitter 211 has semiconductor light emitting devices for emitting light of two different wavelengths $\lambda 1$, $\lambda 2$, respectively. For instance, one of the semiconductor light emitting devices is a red LED 211R for emitting red LED light of the wavelength $\lambda 1$ in a red wavelength range, and the other one thereof is an infrared LED 211IR for emitting infrared LED light of the wavelength $\lambda 2$ in an infrared wavelength range. The light detector 212 has a photoelectric conversion device for generating an electric current in accordance with an intensity of light emitted from the light emitter 211. An example of the photoelectric conversion device is a silicon photo diode having photosensitivity to at least the wavelengths $\lambda 1$ and $\lambda 2$.

As shown in FIG. 5, the light emitter 211 and the light detector 212 are juxtaposed with respect to the finger F for measurement, i.e., living tissue from which the blood oxygen saturation is to be measured. For instance, on the tip of the finger F where a pulse beat of the arterial blood is easily detected optically, the light emitter 211 is arranged adjacent the nail portion of the finger tip, and the light detector 212 is arranged adjacent the ball portion of the finger tip. In an actual measurement, fixedly holding the finger F by the probe 21 enables to dispose the light emitter 211 and the light detector 212 at the aforementioned positions. Alternatively, a medicated tape such as a surgical tape or a first-aid adhesive tape may be used to securely position the light emitter 211 and the light detector 212 with respect to the finger F. By the above attachment, the light of the wavelengths $\lambda 1$, $\lambda 2$ which has passed through the finger F is detected by the light detector 212.

The light emitter 211 and the light detector 212 are respectively connected to a light emitting circuit 211C and a light detecting circuit 212C. The light emitting circuit 211C and the light detecting circuit 212C are fabricated in the oximeter main body 200. The light emitter 211 and the light detector 212 are electrically connected to the light emitting circuit 211C and the light detecting circuit 212C, respectively, by way of the probe cable 205.

An operation of the light emitting circuit 211C is controlled by a microprocessor 20C so that a specified emission control signal is issued to the red LED 211R and to the infrared LED 211IR of the light emitter 211. When the emission control signal is issued to the red LED 211R and to the infrared LED 211IR, for instance, the red LED 211R and the infrared LED 211IR are alternately driven, and red light and infrared light are alternately emitted. Also, the light detecting circuit 212C is controlled in synchronism with the emission of the light emitter 211 by the microprocessor 20C to generate an electric current signal, i.e., a pulse signal, which is obtained by photoelectrical conversion of the received light in accordance with the received light intensity.

Oxygen is transported by oxidation/reduction of hemoglobin in the blood. The hemoglobin has such optical characteristics that absorption of red light is decreased, and absorption of infrared light is increased when the hemoglobin is oxidized, and, conversely, absorption of red light is increased and absorption of infrared light is decreased when the hemoglobin is reduced. It is possible to obtain the blood oxygen saturation, i.e., an arterial blood oxygen saturation by measuring a variation in transmitted light amounts of the red light and the infrared light, which is detected by the light detecting circuit 212C, by utilizing the optical characteristics.

Figure 6A:
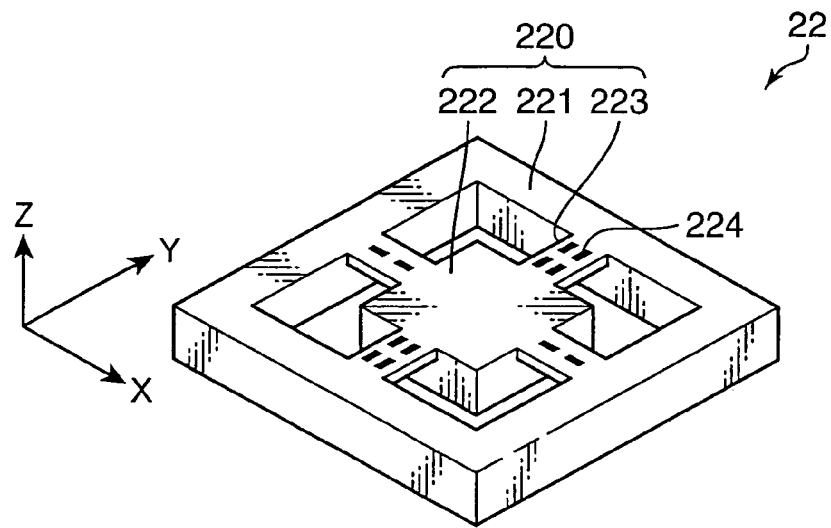
Figure 6B:
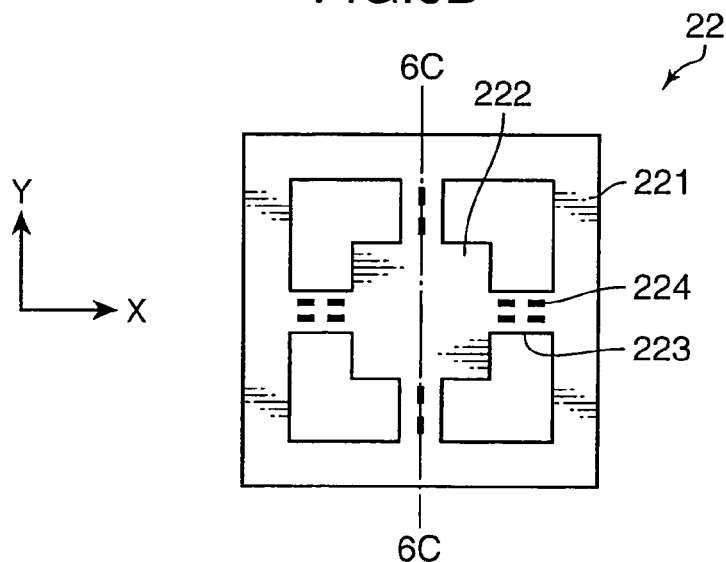
Figure 6C:
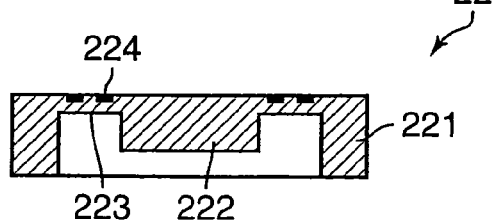

In the following, the three-axis acceleration sensor 22 built in the oximeter main body 200 is described. FIGS. 6A through 6C are illustrations showing a three-axis acceleration sensor using a piezoresistor, as an example of the three-axis acceleration sensor. FIG. 6A is a perspective view of the three-axis acceleration sensor 22, FIG. 6B is a top plan view thereof, and FIG. 6C is a cross-sectional view taken along the line 6C-6C in FIG. 6B. The three-axis acceleration sensor 22 is constructed utilizing a piesoresistive effect. The piezoresistive effect is such that when a mechanical external force is exerted to an object composed of a semiconductor material having a piezo effect, crystal lattice distortion occurs in the object, and the number of carriers or carrier moving degree in the object is varied, which causes a change in resistance of the object.

The three-axis acceleration sensor 22 includes a sensor body 220 and twelve piezoresistive devices 224. The sensor body 220 has a four-sided frame-like support 221 formed by dry-etching a base material such as silicon, a weight portion 222 disposed in the middle of the support 221, and thin beam portions 223 each for connecting a corresponding side portion of the support 221 to the weight portion 222. The twelve piezoresistive devices 224 are attached to the beam portions 223, as shown in FIG. 6A, for instance. When the weight portion 222 is vibrated by application of acceleration, the beam portions 223 are deformed, and a stress is applied to the piezoresistive devices 224.

Specifically, when an external force is exerted on the three-axis acceleration sensor 22, namely, when a vibration or a tilting force resulting from a body motion of the subject is exerted on the oximeter main body 200, the weight portion 222 is deformed about X-axis, Y-axis, or Z-axis (see FIG. 6A) depending on the body motion, thereby deforming the beam portions 223. Then, a stress is applied to the piezoresistive devices 224 depending on the degree of the deformation of the beam portions 223, and, as a result, the resistances of the piezoresistive devices 224 are varied depending on the application of the stress. Thus, oscillation of the oximeter main body 200, i.e., the body motion of the subject is detected by detecting variations in resistance of the piezoresistive devices 224, which are signals proportional to acceleration.

The acceleration-proportional signals regarding the piezoresistive devices 224 can be detected by constituting a Wheatstone bridge circuit of four piezoresistive devices 224 each for the X-axis, Y-axis, and Z-axis, namely, using the twelve piezoresistive devices 224 in total, and by detecting respective variations in resistance resulting from application of stress to the piezoelectric devices 224 as a voltage change. In this embodiment, an axis output of either one of the X-, Y-, and Z-axes is used to detect a body motion of the subject. Alternatively, two axis outputs among the X-, Y-, and Z-axes, or all the three axis outputs may be used.

(Description on Electrical Configuration)

Figure 7:
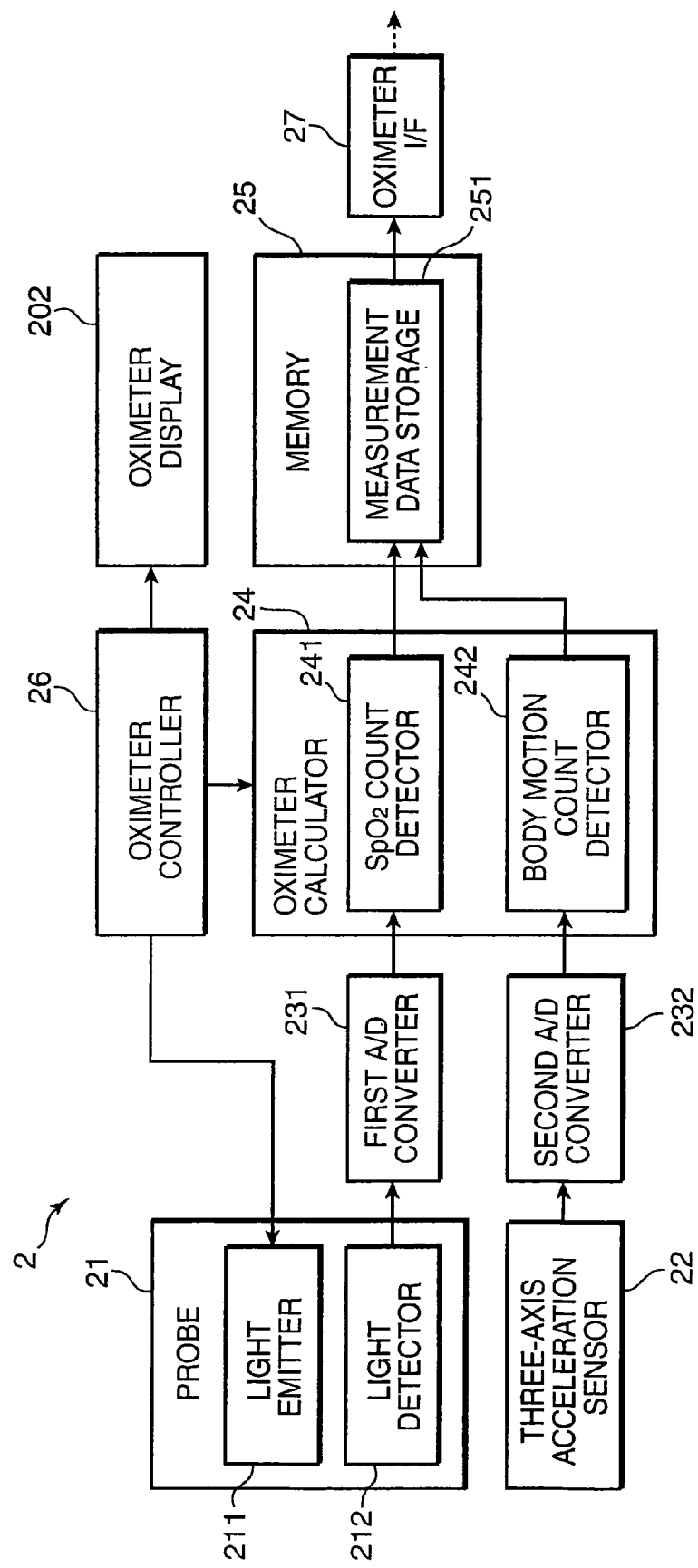
FIG. 7 is a block diagram of an arrangement showing electrical functions of the pulse oximeter.

FIG. 7 is a block diagram of an arrangement showing electrical functions of the pulse oximeter 2. The pulse oximeter 2 includes a first A/D converter 231, a second A/D converter 232, an oximeter calculator 24, a memory 25 serving as the storage, an oximeter controller 26, and an oximeter interface (I/F) 27 in addition to the oximeter display 202, the probe 21 serving as the blood oxygen saturation detector, and the three-axis acceleration sensor 22 serving as the body motion detector.

As mentioned above, the probe 21 has the light emitter 211 and the light detector 212 to detect blood oxygen saturation information of the subject. Also, the three-axis acceleration sensor 22 detects body motion information concerning the body motion of the subject.

An analog current signal outputted from the light detector 212 at a predetermined sampling frequency in accordance with the transmitted amounts of red light and infrared light is converted into a voltage signal by a current/voltage converting circuit (not shown), and the voltage signal is converted into a digital signal by the first A/D converter 231. Similarly, respective output values, i.e., analog current signals from the three-axis acceleration sensor 22 with respect to the X-, Y-, and Z-axes are converted into voltage signals after current-to-voltage conversion, and then these voltage signals are converted into digital signals by the second A/D converter 232.

The oximeter calculator 24 is a functioning part for obtaining count values concerning blood oxygen saturation ($SpO_2$) and body motion based on the digital measurement signals outputted from the first A/D converter 231 and from the second A/D converter 232, respectively. The oximeter calculator 24 includes an $SpO_2$ count detector 241, and a body motion count detector 242.

The $SpO_2$ count detector 241 detects a count value corresponding to $SpO_2$ every predetermined cycle, e.g., every one second in response to receiving the digital measurement signal from the first A/D converter 231 at a fixed interval. The body motion count detector 242 detects a count value corresponding to a body motion in one of the X-, Y-, and Z-axes every predetermined cycle in response to receiving the digital measurement signal from the second A/D converter 232 at a fixed interval.

The memory 25 includes a RAM or a like device for storing various setting information, and has a measurement data storage 251. The measurement data storage 251 temporarily stores the measurement data acquired by the probe 21 and by the three-axis acceleration sensor 22, i.e., the count values corresponding to the respective measurement data in association with the time when the respective data have been acquired.

The oximeter controller 26 controls sensing operations by the probe 21, i.e., the light emitter 211 and the light detector 212, and by the three-axis acceleration sensor 22, an operation of calculating the count values by the oximeter calculator 24, and an operation of writing the count values into the memory 25. Specifically, the oximeter controller 26 causes the probe 21 and the three-axis acceleration sensor 22 to acquire the measurement data concerning $SpO_2$ and body motion of the subject at the predetermined sampling frequency, causes the oximeter calculator 24 to calculate the respective count values corresponding to the measurement data, and causes the memory 25 to store the obtained count values therein.

The oximeter I/F 27 is an interface for connecting the PC 3 and the pulse oximeter 2 for data communication. Specifically, the oximeter I/F 27 functions as an interface for downloading the count values corresponding to the measurement data stored in the memory 25 of the pulse oximeter 2 to the PC 3.

Figure 8:
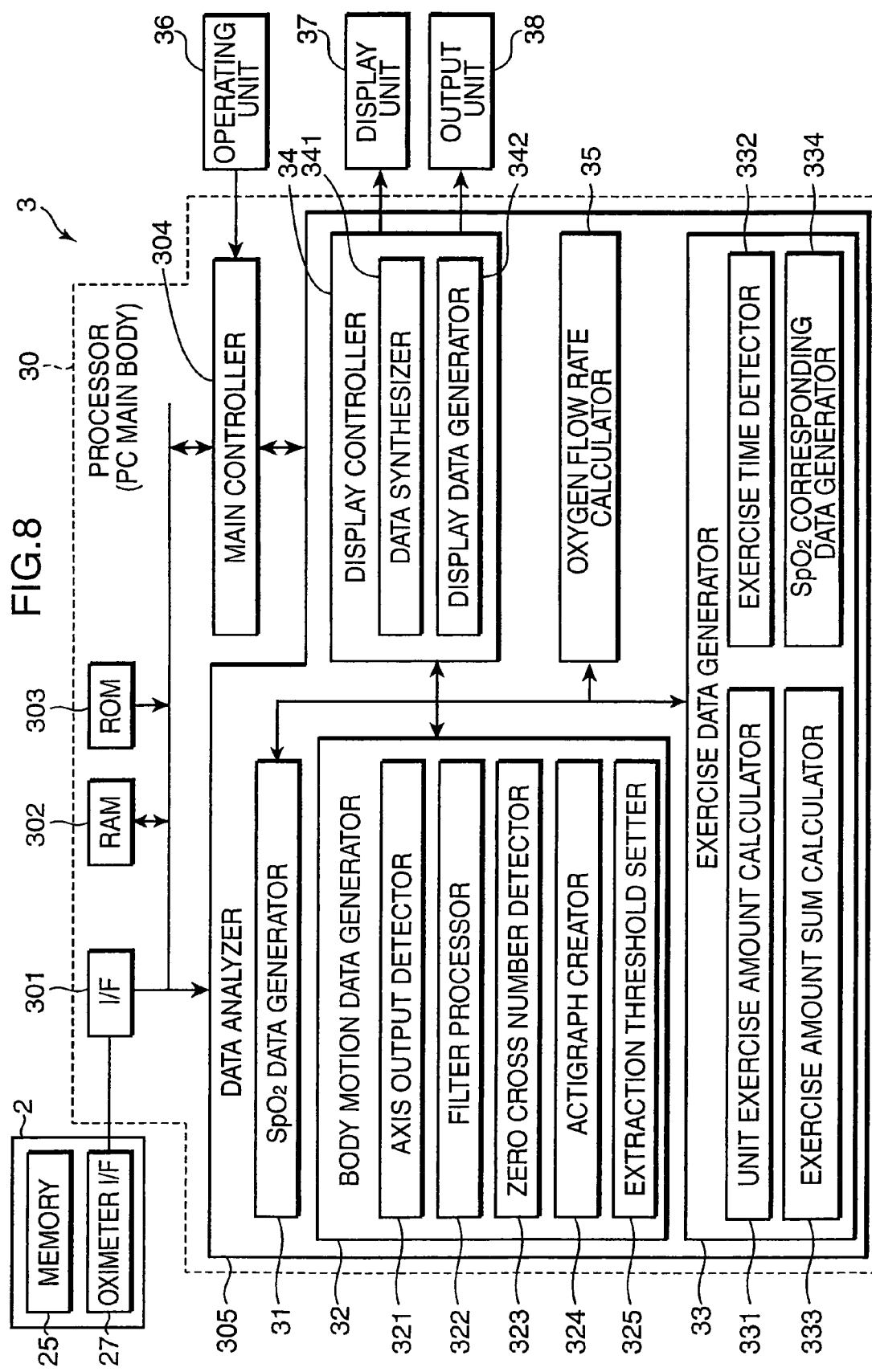
FIG. 8 is a block diagram of an arrangement showing electrical functions of a PC main body, i.e., an analyzer or a processor.

FIG. 8 is a block diagram of an arrangement primarily showing electrical functions of the PC main body 30, i.e., an analyzer or a processor of the PC 3. The PC main body 30 includes a PC interface (I/F) 301, an RAM 302, an ROM 303, a main controller 304, and a data analyzer 305.

The PC I/F 301 is an interface for connecting the PC main body 30 to the pulse oximeter 2 for data communication. The RAM 302 temporarily stores therein the measurement data downloaded from the memory 25 of the pulse oximeter 2, and various data acquired in the respective parts of the PC main body 30. The ROM 303 stores therein an operation program product for operating the PC main body 30 or the oximeter system S. The main controller 304 causes the data analyzer 305 to analyze the measurement data stored in the RAM 302 by temporarily storing the measurement data into the RAM 302 or by reading out the operation program product from the ROM 303.

The data analyzer 305 generates analysis data concerning a relation between respiratory disease presentation and body motion of the subject by analyzing a relation between change in blood oxygen saturation and body motion of the subject based on the measurement data concerning the blood oxygen saturation information and the body motion information, and generates display data for displaying the analysis data on the display unit 37. The data analyzer 305 includes an $SpO_2$ data generator 31, a body motion data generator 32, an exercise data generator 33, a display controller 34, and an oxygen flow rate calculator 35.

The $SpO_2$ data generator 31 is a functioning part for generating time-based data on $SpO_2$ value resulting from a respiratory failure of the subject. The $SpO_2$ data generator 31 creates the time-based data on the $SpO_2$ value, i.e., an $SpO_2$ curve by expressing count values corresponding to the $SpO_2$, which have been acquired from the measurement data storage 251 of the memory 25 of the pulse oximeter 2 in association with the data acquired time, along a time axis.

Figure 9:
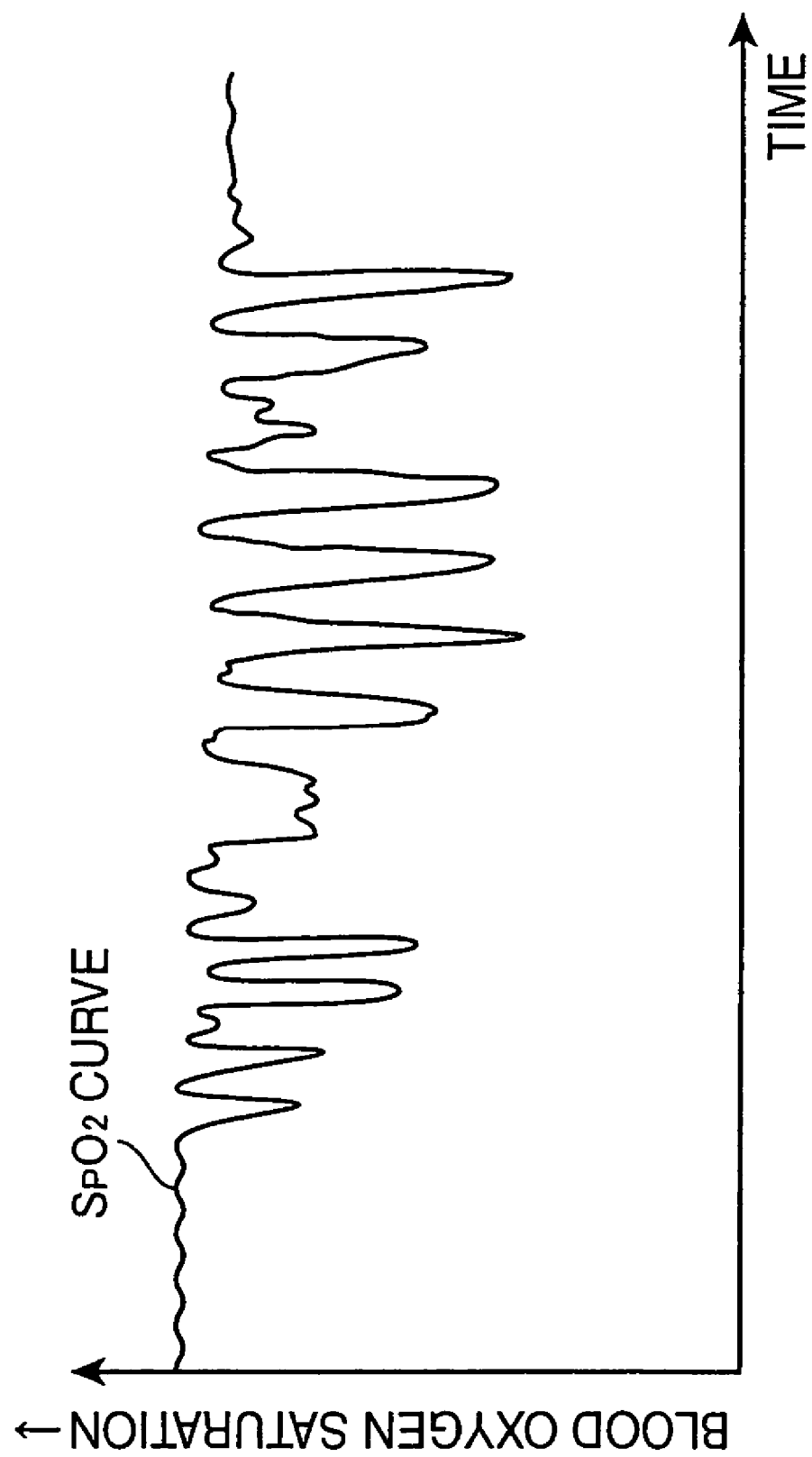
FIG. 9 is a graph showing an example of an $SpO_2$ curve.

FIG. 9 is a graph showing an example of the $SpO_2$ curve. As illustrated in FIG. 9, expressing the $SpO_2$ count values acquired at the predetermined sampling frequency along the time axis enables to obtain one $SpO_2$ curve with respect to the subject. In the case where a respiratory failure appears in the subject a certain number of times during the measurement, the $SpO_2$ value is lowered accordingly. In other words, the $SpO_2$ curve shows a plurality of peaks where the $SpO_2$ value is temporarily lowered. Hereinafter, a peak point where the $SpO_2$ shows a lowest value is called "$SpO_2$ lowest peak". It is possible to recognize presentation of respiratory failure based on the $SpO_2$ lowest peaks. However, it is impossible to judge whether such a respiratory failure has a correlation to body motion of the subject based on the above data analysis.

The body motion data generator 32 is a functioning part for calculating data concerning a time-based change of body motion of the subject during the measurement. The body motion data generator 32 includes an axis output detector 321, a filter processor 322, a zero-cross number detector 323, an actigraph creator 324, and an extraction threshold setter 325.

The axis output detector 321 obtains data concerning a time-based change of oscillation of one of the X-, Y-, and Z-axes of the three-axis acceleration sensor 22 by expressing a count value, i.e., an output voltage representing the oscillation, i.e., a tilt angle of the corresponding axis of the three-axis acceleration sensor 22 acquired from the measurement data storage 251 of the memory 25 of the pulse oximeter 2, along a time axis. Alternatively, the axis output to be extracted may be arbitrarily changed, or plural axis outputs may be used by executing a 24-hour continuous pulse oximetry or by executing an overnight pulse oximetry.

Figure 10:
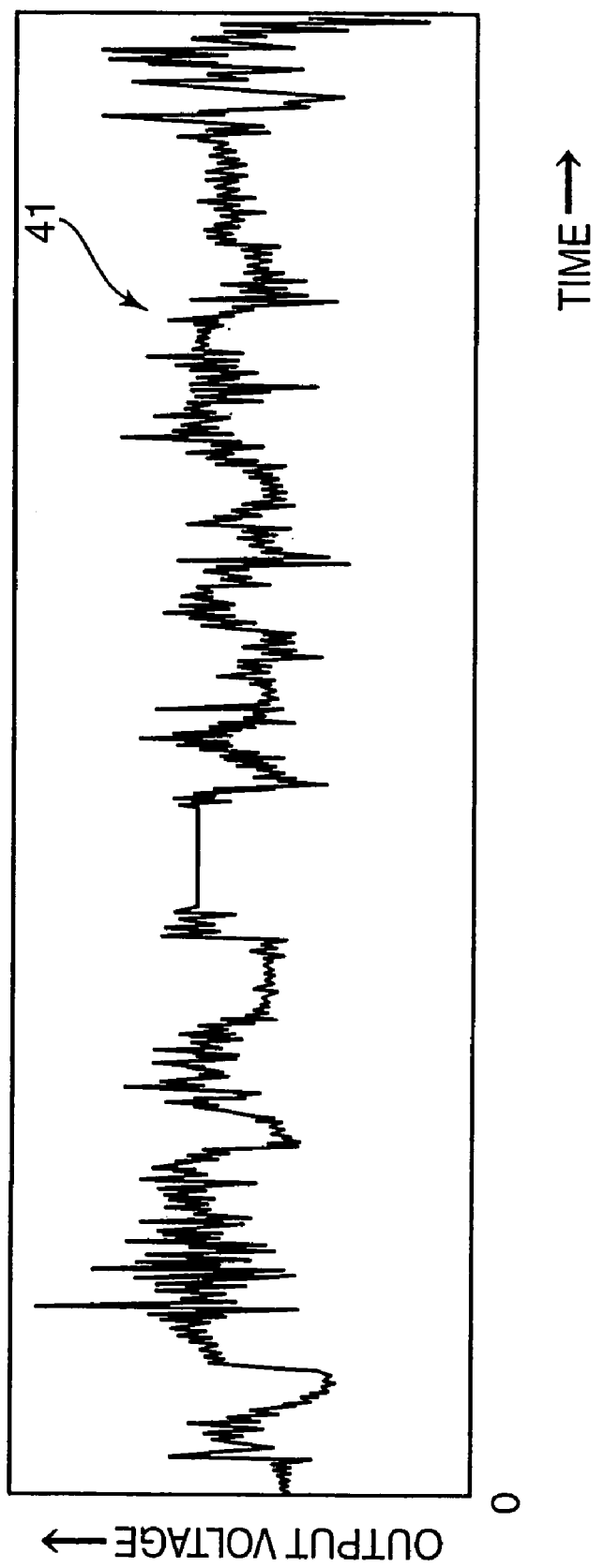
FIG. 10 is a graph showing an example of a body motion curve.

FIG. 10 is a graph showing an example of a body motion curve 41, which represents a time-based change of the output voltage of the three-axis acceleration sensor 22 detected by the axis output detector 321. In the body motion curve 41 in FIG. 10, a flat portion corresponds to a time zone when a body motion of the subject has not been detected, and a portion of a sharp gradient corresponds to a time zone when a large body motion of the subject has been detected.

The filter processor 322 includes a digital filter, and performs filter processing of extracting a data component having a close relation to a body motion from the body motion curve 41 obtained by the axis output detector 321. Specifically, the filter processor 322 removes low-frequency and high-frequency signal components by sending the output voltage of the three-axis acceleration sensor 22 to a band-pass filter capable of passing signals in the range of about 2 to 3 Hz, which has a close relation to the body motion. This arrangement enables to remove a noise component or the like from the body motion curve 41.

Figure 11:
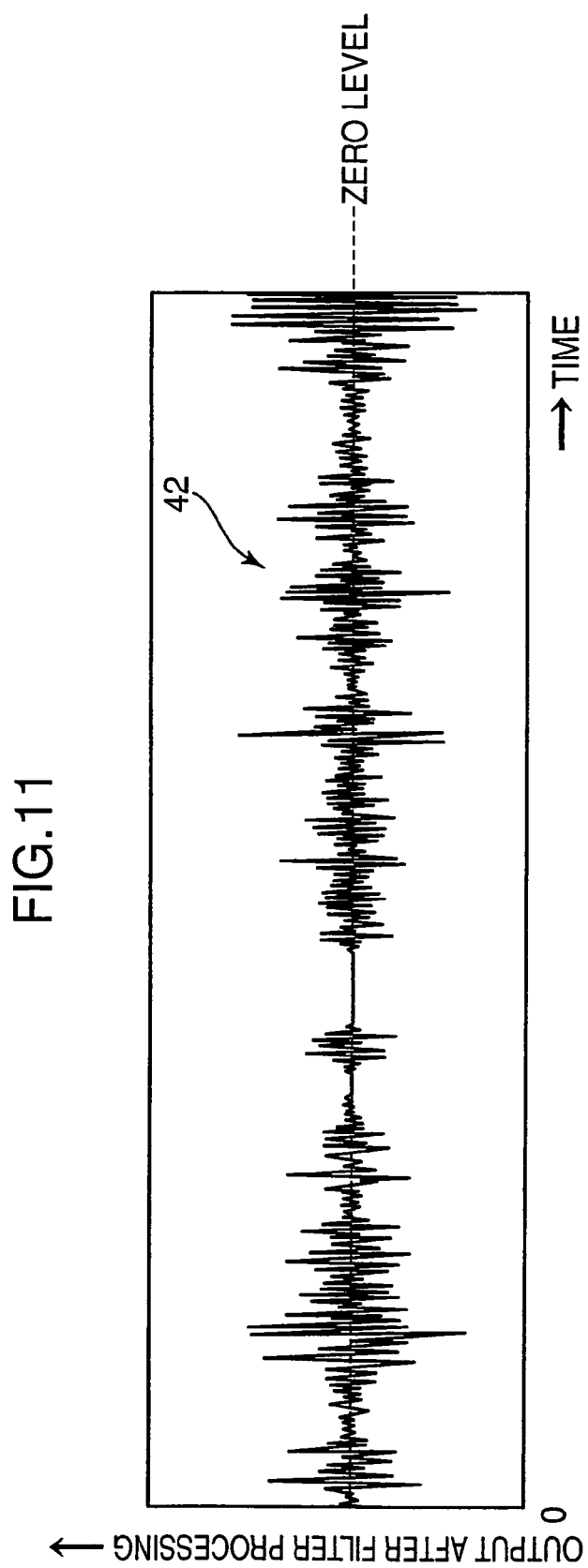
FIG. 11 is a graph showing an example of a body motion curve after filter processing.

FIG. 11 is a graph showing a body motion curve 42 after the filter processing by the filter processor 322. The body motion curve 42 is obtained by converting the body motion curve 41 into pulse information in the range of about 2 to 3 Hz, with zero level defined as an oscillation baseline. The frequency characteristic of the band-pass filter may be arbitrarily changed depending on the physical constitution, the age, or a like factor of the individual subjects.

Figure 12:
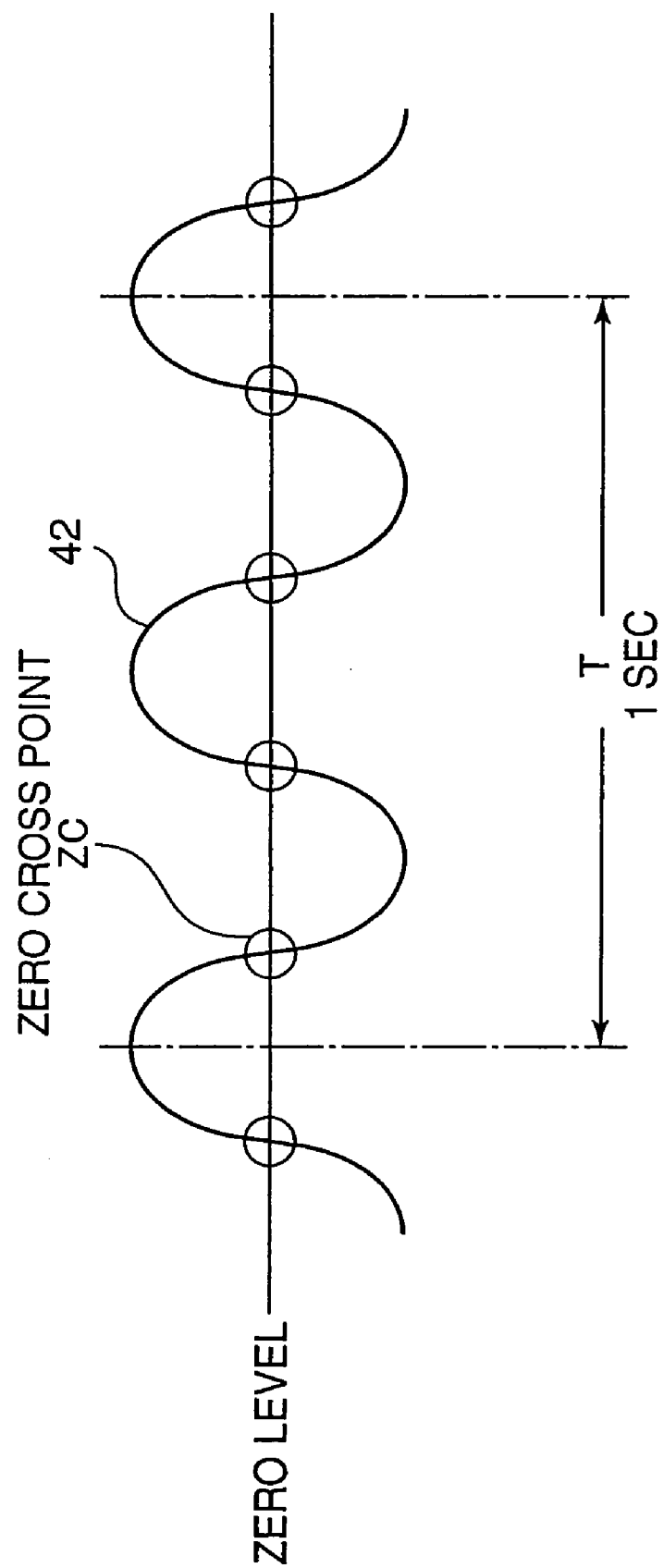
FIG. 12 is an illustration showing a principle as to how the number of zero cross points is counted.

The zero-cross number detector 323 counts the number of times when the body motion curve 42 crosses the zero level at a certain detection time interval T, as shown in FIG. 12, to quantitize the body motion information of the subject. As shown in the example of FIG. 12, the detection time interval T is one second, and the zero-cross point ZC at which the body motion curve 42 crosses the zero level appears four times within the detection time interval T. Accordingly, the zero-cross number detector 323 detects the zero-cross number=4 within the detection time interval T. The counting is carried out successively along the time axis of the body motion curve 42 shown in FIG. 11. As a result of the counting, zero-cross number information acquired at the detection time interval T is obtained for the time zone when the pulse oximetry has been executed.

The actigraph creator 324 creates data information, i.e., graph information with which a user can easily recognize the time-based change of the body motion or the exercise amount of the subject by expressing the zero-cross number information acquired by the zero-cross number detector 323 along a time axis. In this embodiment, the zero-cross number is used as an element for creating the actigraph. Alternatively, it is possible to adopt a threshold method of counting the number of times of appearance of a detection value which exceeds a predetermined threshold value in the body motion curve 42 shown in FIG. 11, or an integration method of integrating the output signals of the three-axis acceleration sensor 22. In both of the methods, an actigraph can be created by expressing the threshold excessive count value or the integrated value along a time axis.

Figure 13:
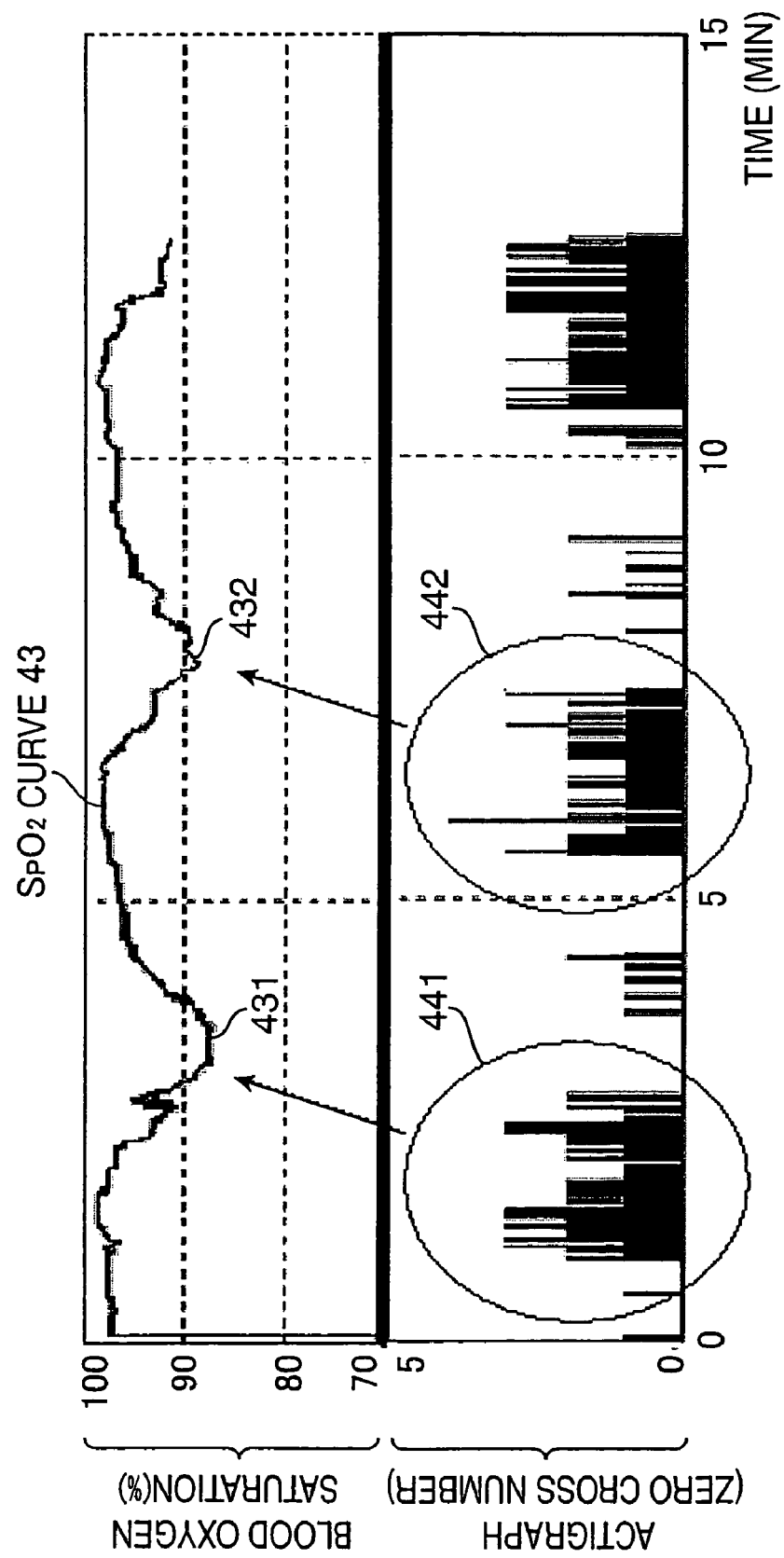
FIG. 13 is a graph showing an example of a composite graph generated by combing an $SpO_2$ curve and an actigraph.

FIG. 13 is a graph showing an example of the actigraph created by the actigraph creator 324. In the graph of FIG. 13, an $SpO_2$ curve 43 is expressed together with the actigraph along a common time axis. The composite graph as shown in FIG. 13 is created by the display controller 34, which will be described later. The actigraph in FIG. 13 is an example of a bar graph representing the zero-cross numbers detected at the certain detection time interval T (=1 sec.). Likewise, the $SpO_2$ curve 43 is a line graph created based on a detection value of the $SpO_2$ every one second. The actigraph estimatively shows that a body motion of the subject does not appear, in other words, an exercise has not been conducted in the time zone when the zero-cross numbers are not sequentially detected, and that a continuous body motion of the subject appears, namely, a continuous exercise has been conducted in the time zone when the zero-cross numbers are sequentially detected.

For instance, in the actigraph shown in FIG. 13, the time zones indicated by circles 441, 442 represent significant exercise time zones when the zero-cross numbers are sequentially detected. It is estimated that an exercise such as a continuous walk has been conducted in the time zone of about several minutes. On the other hand, the $SpO_2$ curve 43 shown in FIG. 13 clearly shows that there exist two $SpO_2$ lowest peaks 431, 432, which fall below the $SpO_2$ value of 90%. Thus, the user is enabled to recognize a correlation between the $SpO_2$ lowest peaks 431, 432, and the exercise time zones 441, 442 at a glance of the composite graph in FIG. 13.

In this way, the user can recognize the correlation between exercise and time-based change of $SpO_2$ value of the subject. There is a tendency that a patient under application of the home oxygen therapy (HOT) shows lowering of the $SpO_2$ value after an exercise of a certain period. The graph in FIG. 13 shows that the lowest peak 431 appears immediately after the exercise time zone 441, and that the lowest peak 432 appears immediately after the exercise time zone 442. Accordingly, the graph shows that there is a close relation between exercise and time-based change of $SpO_2$ value, i.e., lowering of $SpO_2$ value, which enables a medical staff to readily diagnose that the subject is suspected to have a symptom peculiar to a patient under application of the HOT.

Figure 14:
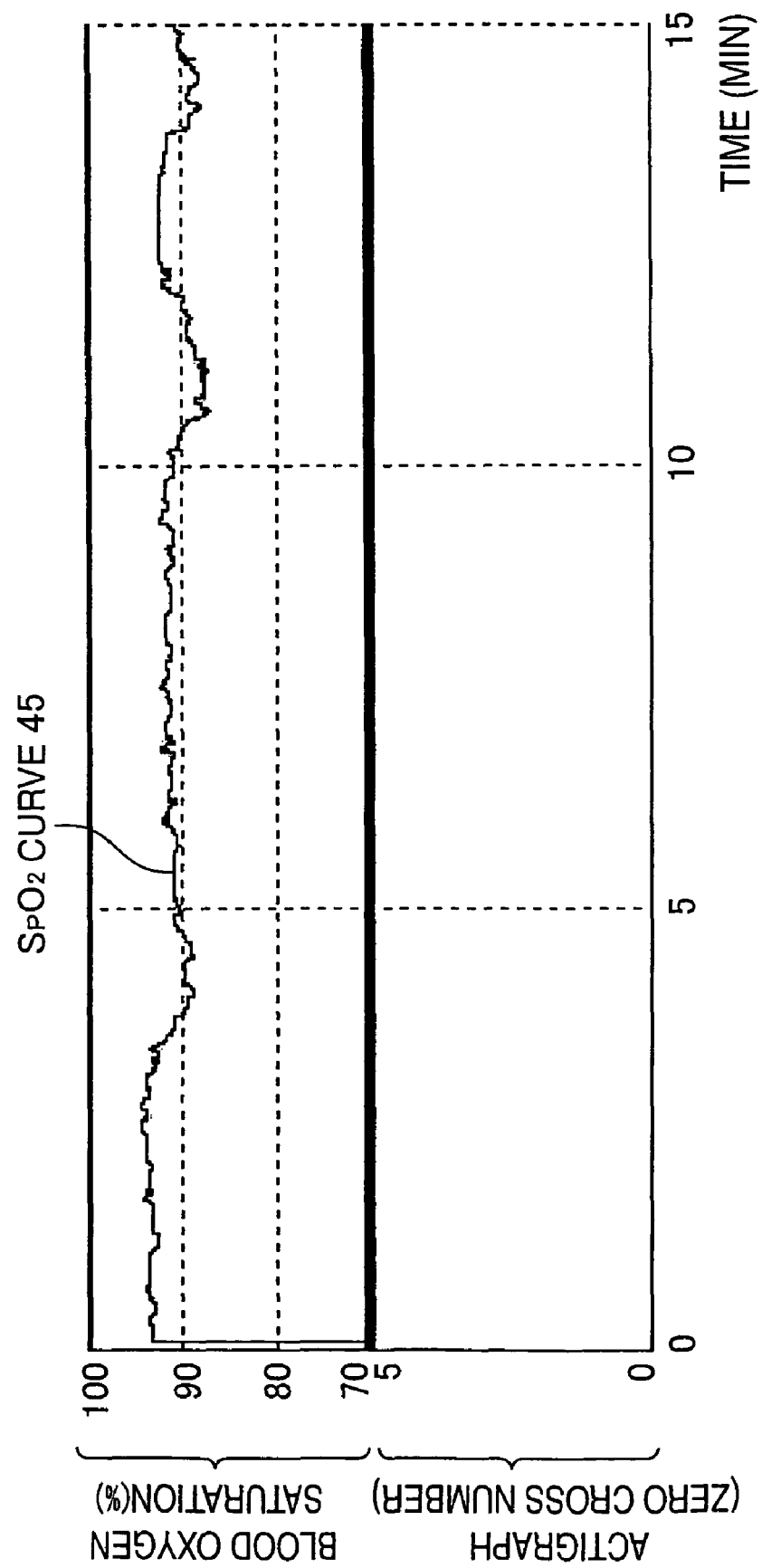
FIG. 14 is a graph showing another example of a composite graph generated by combing an $SpO_2$ curve and an actigraph.

In the case where a graph as shown in FIG. 14 is obtained, for instance, at a glance of the graph, the user is enabled to recognize that a lowest peak lower than the $SpO_2$ value of 90% appears in an $SpO_2$ curve 45, despite the fact that the zero-cross number is not detected in the actigraph of FIG. 14. In this case, it is obvious that there is no relation between exercise and time-based change of $SpO_2$ value, i.e., lowering of $SpO_2$ value. The lowering of $SpO_2$ value is due to likelihood that the subject's performance of exhausting carbon dioxide gas is temporarily weakened while the subject is at rest or in sleep. In such a condition, the medical staff can diagnose that the subject is suspected to be a patient in need of NIPPV.

In this way, at least a correlation between exercise and time-based change of $SpO_2$ value of the subject can be readily recognized by creating an actigraph by the actigraph creator 324, creating an $SpO_2$ curve by the $SpO_2$ data generator 31, and by expressing the actigraph and the $SpO_2$ curve along a common time axis. Thereby, a judgment on a therapeutic approach as to whether the HOT should be used or the NIPPV should be used can be easily made.

Referring back to FIG. 8, the extraction threshold setter 325 is a functioning part for accepting various setting values in extracting data concerning body motion of the subject. For instance, the extraction threshold setter 325 accepts designation to change the band-pass filter characteristics in the filter processor 322, the detection time interval T (see FIG. 12) in the zero-cross number detector 323, or the like depending on the individual subjects. Also, the extraction threshold setter 325 accepts designation to change various setting values to be used in the processing by the exercise data generator 33, which will be described later, e.g., an exercise time count start/end parameter, depending on the individual subjects.

The exercise data generator 33 is a functioning part for performing data presentation and data analysis in association with the exercise to recognize a correlation between exercise and time-based change of $SpO_2$ value in detail. Specifically, the exercise data generator 33 generates analysis data capable of displaying at least the following two relations (a), (b) in association with the exercise in terms of a graph or like means, so that a targeted oxygen flow rate capable of maintaining the $SpO_2$ value at 90% or more throughout all the measurement time of the subject including a rest time, a sleeping time, and an exercise time, with use of a therapeutic apparatus such as a home oxygen therapy, for instance, can be determined.

(a) a relation between exercise amount and lowest peak of $SpO_2$ and (b) a relation between exercise time and lowest peak of $SpO_2$ The exercise data generator 33 includes a unit exercise amount calculator 331, an exercise time detector 332, an exercise amount sum calculator 333, and an $SpO_2$ corresponding data generator 334 to obtain the relations (a) and (b).

The unit exercise amount calculator 331 sequentially calculates a unit exercise amount, which is a summation of body motion information for a certain unit time, based on the measurement data concerning the body motion information, by sequentially advancing the time along the time axis. In this embodiment, the body motion information represents the zero cross number detected by the zero cross number detector 323 at the detection time interval T=1 sec. Let it be assumed that the zero cross number at the detection time interval T is defined as a per-second exercise amount Ws. The unit exercise amount calculator 331 calculates a unit exercise amount (hereinafter, called as "per-minute exercise amount Wm") by summing the per-second exercise amounts Ws for a certain unit time e.g. one minute.

The per-minute exercise amount Wm is sequentially calculated by sequentially advancing the time along the time axis. For instance, a per-minute exercise amount Wm at the point of time t1 is obtained as the sum of sixty per-second exercise amounts Ws, which are obtained for a time duration of 60 seconds before the point of time t1. Similarly, another per-minute exercise amount Wm at the point of time t2(=t1+1 sec.) is calculated as the sum of sixty per-second exercise amounts Ws, which are obtained for a time duration of 60 seconds before the point of time t2. Thus, the per-minute exercise amounts Wm are sequentially calculated. This is because the $SpO_2$ value is not lowered immediately after an exercise, and there is a time lag between the point of time when the $SpO_2$ value is lowered, and the point of time when the exercise is conducted. Accordingly, it is proper to calculate an exercise amount for a certain unit time before the point of time when an instant $SpO_2$ value, i.e., a per-second $SpO_2$ value has been acquired in order to evaluate a correlation between the exercise amount and the instant or the per-second $SpO_2$ value.

To summarize the above calculation, the per-minute exercise amount Wm corresponding to the per-second $SpO_2$ value can be obtained by implementing the mathematical formula (1) based on the per-second exercise amounts Ws. The summation unit of the unit exercise amount is not limited to one minute. Alternatively, the summation unit of the unit exercise amount may be arbitrarily changed depending on the individual subjects, and may be an item to be set in the extraction threshold setter 325.

$$Wm(i) = \sum_{j=-60}^{0} Ws(i+j) \qquad (1)$$

Figure 15:
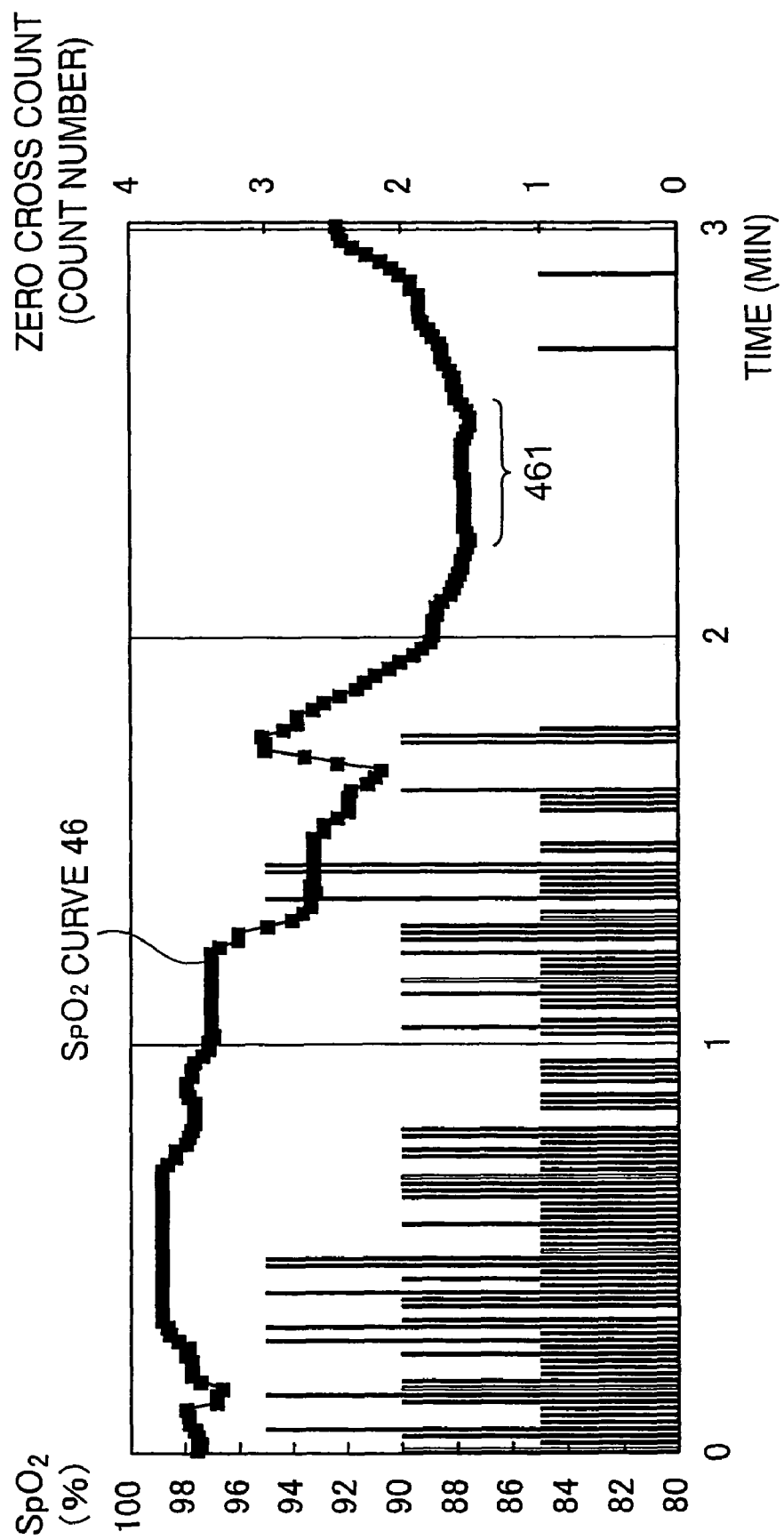
FIG. 15 is a graph, in which $SpO_2$ values and an actigraph are plotted every one second for three minutes.

FIG. 15 is a graph, in which $SpO_2$ values and an actigraph, i.e., the zero cross numbers, which have been measured with respect to a subject for three minutes, are plotted every one second, namely, a graph showing a correlation between the per-second $SpO_2$ values and the per-second exercise amounts Ws. The $SpO_2$ values are expressed as a line graph, in other words, are displayed as an $SpO_2$ curve 46. The zero cross numbers are expressed as a bar graph. The graph in FIG. 15 is similar to the graph shown in FIG. 13. At a glace of the graph in FIG. 15, it is confirmed that there is a close relation between exercise and lowering of $SpO_2$ value because a lowest peak 461 appears in the $SpO_2$ curve 46 immediately after a certain exercise has been conducted. However, it is difficult or impossible to elucidate at what degree of the exercise the $SpO_2$ value is lowered.

Figure 16:
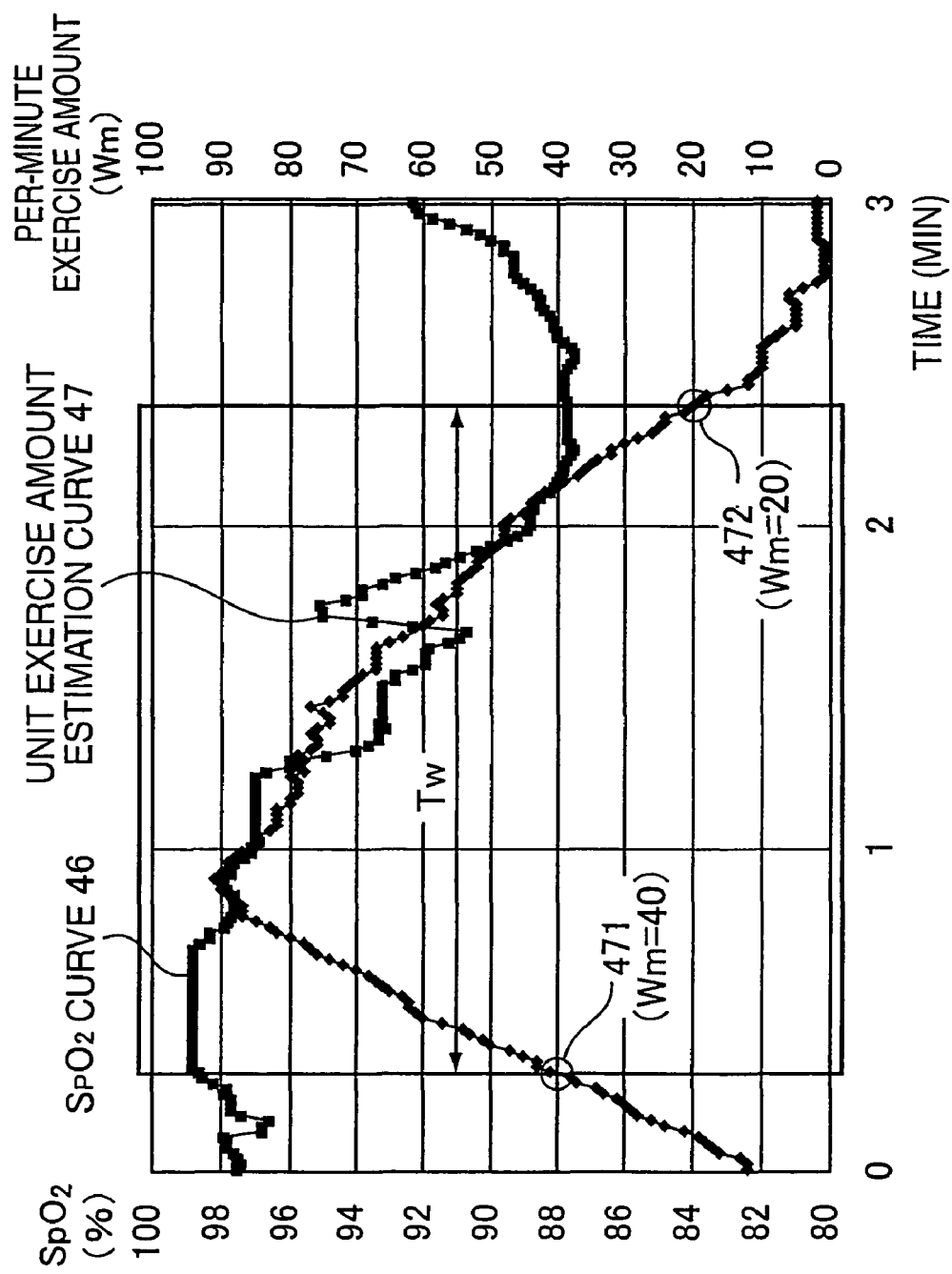
FIG. 16 is a graph, in which a unit exercise amount estimation curve, i.e., a line graph regarding per-minute exercise amount Wm, and the $SpO_2$ curve shown in FIG. 15 are expressed along a common time axis.

FIG. 16 is a graph, in which a unit exercise amount estimation curve 47, i.e., a line graph in which the per-minute exercise amounts Wm obtained by the unit exercise amount calculator 331 are expressed, and the $SpO_2$ curve 46 shown in FIG. 15 are displayed along a common time axis. The display data as shown in FIG. 16 is generated by the display controller 34, which will be described later. The graph in FIG. 16 shows that the $SpO_2$ value starts to be lowered when the per-minute exercise amount Wm exceeds a predetermined count number, and conversely, starts to be raised or recovered when the per-minute exercise amount Wm is equal to or lower than the predetermined count number. Accordingly, it is possible to recognize a symptom peculiar to the subject, namely, to know the exercise limit at which the $SpO_2$ value starts to be lowered by comparing the calculation result of the unit exercise amount calculator 331 with the $SpO_2$ curve. In this way, the correlation between exercise and lowering of $SpO_2$ value can be analyzed in detail by merely obtaining the unit exercise amount estimation curve 47. In addition to the above arrangement, in this embodiment, the exercise time detector 332, the exercise amount sum calculator 333, and the $SpO_2$ corresponding data generator 334 are provided to perform further detailed analysis.

The exercise time detector 332 determines an exercise time, which is a time zone when a significant exercise is presumed to have been conducted, based on the measurement data concerning the body motion information with use of a predetermined reference value. In this embodiment, the point of time when the per-minute exercise amount Wm reaches 40 counts is defined as an exercise time count start point of time 471, and the point of time when the per-minute exercise amount Wm equals 20 counts or less is defined as an exercise time count end point of time 472, based on the unit exercise amount estimation curve 47. A time duration from the point of time 471 to the point of time 472 is defined as an exercise time Tw. Count values for defining the exercise time count start point of time 471 and the exercise time count end point of time 472, and offset amounts thereof may be arbitrarily set depending on the sex difference, age, physical constitution or a like factor of the individual subjects. Using the exercise time Tw obtained by the exercise time detector 332 enables to recognize a correlation between the length of the exercise time Tw and the lowering of $SpO_2$ value.

The exercise amount sum calculator 333 performs summation of the per-minute exercise amounts Wm for the exercise time Tw detected by the exercise time detector 332. Specifically, in FIG. 16, an exercise amount sum Wa, which is a summation of plotted values on the unit exercise amount estimation curve 47 for the exercise time Tw, is calculated. The calculation of the exercise amount sum Wa enables to estimate the degree of exercise of the subject during the exercise time Tw, which corresponds to a time zone when a significant exercise is presumed to have been performed. Accordingly, this arrangement enables to recognize a correlation between exercise and lowering of $SpO_2$ value based on the analysis of the exercise degree of the subject during the exercise time Tw, in addition to the length of the exercise time Tw. The relation between the exercise amount sum Wa obtained by the exercise amount sum calculator 333, and the per-minute exercise amount Wm can be expressed by the following formula (2).

If Wm>40

While Wm<20, Wa=ΣWm  (2)

The $SpO_2$ corresponding data generator 334 generates corresponding data concerning a correlation between the exercise time Tw obtained by the exercise time detector 332, and the lowest peak of the $SpO_2$ value, or a correlation between the exercise amount sum Wa obtained by the exercise amount sum calculator 333, and the lowest peak of the $SpO_2$ value. The corresponding data generated by the $SpO_2$ corresponding data generator 334 is described in detail referring to FIGS. 17 through 20.

Figure 17:
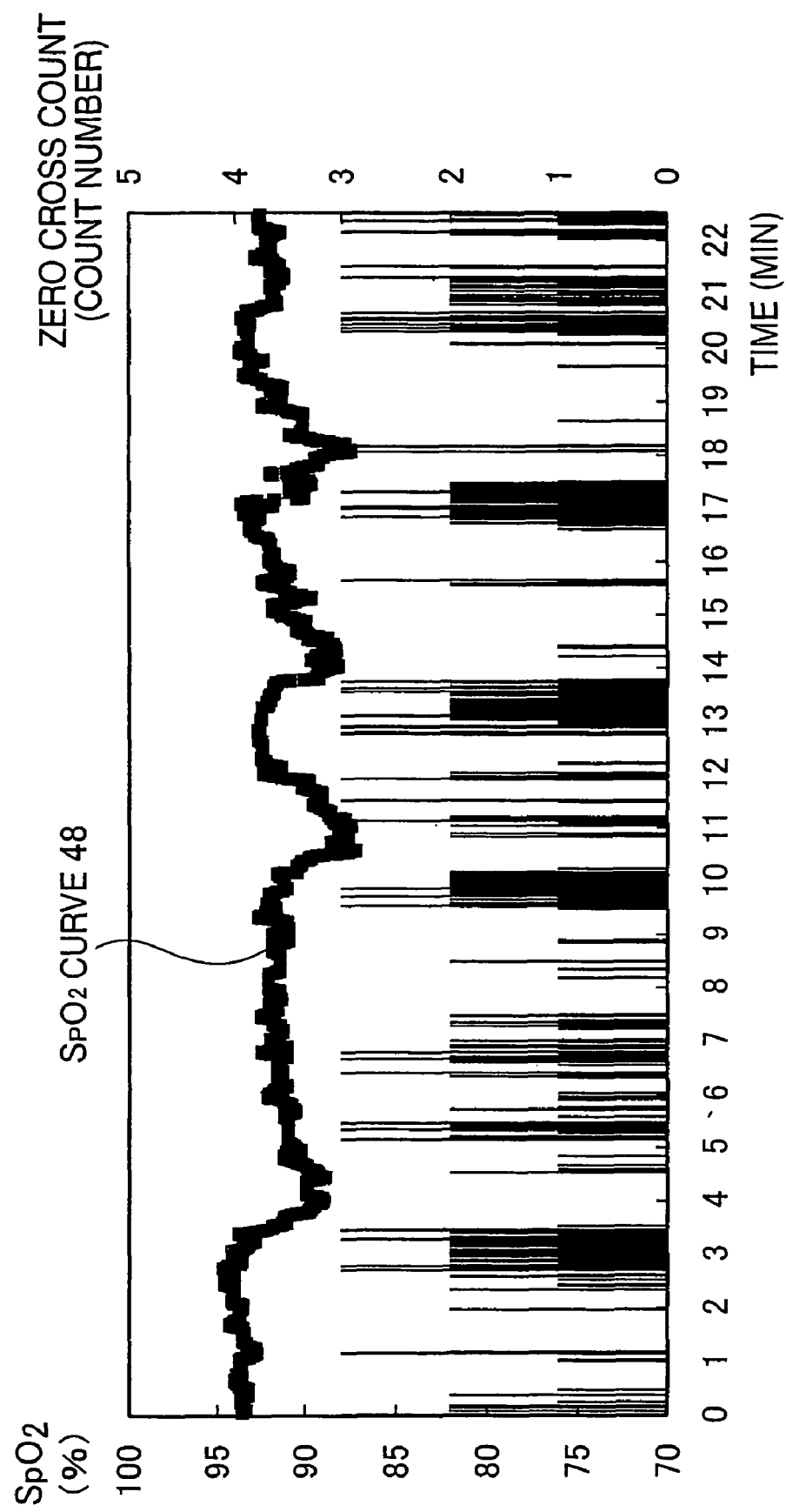
FIG. 17 is a graph, in which per-second $SpO_2$ values and per-second exercise amounts Ws are expressed along a common time axis for twenty-two minutes.

FIG. 17 is a graph, in which per-second $SpO_2$ values, and per-second exercise amounts Ws are detected with respect to a subject for twenty-two minutes. In FIG. 17, the $SpO_2$ values are expressed as a line graph, namely, are displayed as an $SpO_2$ curve 48, and the zero cross numbers are expressed as a bar graph. The graph in FIG. 17 shows that there are several lowest peaks in the $SpO_2$ curve 48, and an exercise is apparently conducted in the measurement time. However, a correlation between exercise and lowering of $SpO_2$ value cannot be elucidated at a glance of the graph in FIG. 17.

Figure 18:
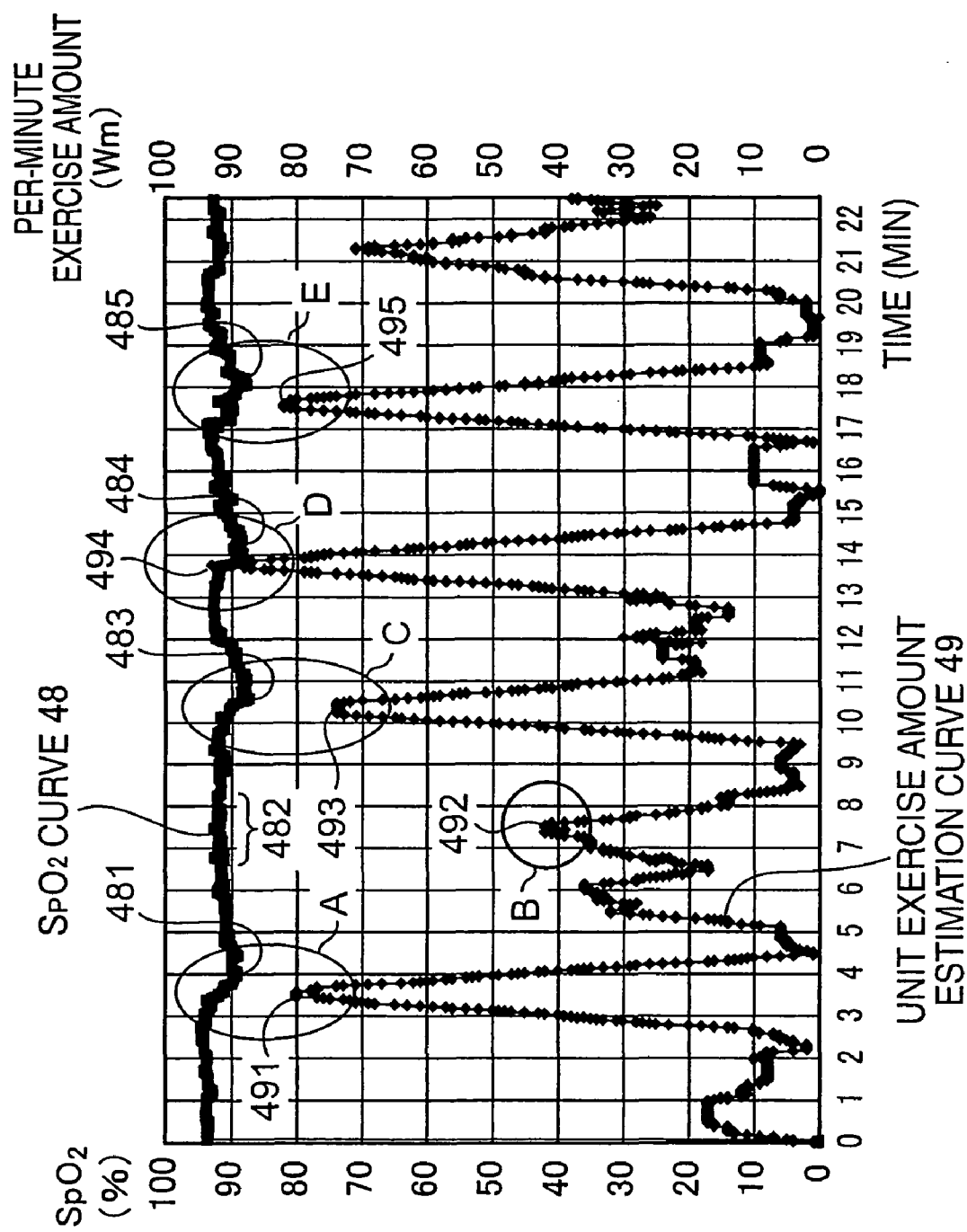
FIG. 18 is a graph, in which a unit exercise amount estimation curve, i.e., a line graph regarding per-minute exercise amount Wm, and the $SpO_2$ curve shown in FIG. 17 are expressed along a common time axis.

FIG. 18 is a graph, in which a unit exercise amount estimation curve 49, i.e., a line graph in which per-minute exercise amounts Wm obtained by the unit exercise amount calculator 331 are expressed, and the $SpO_2$ curve 48 shown in FIG. 17 are displayed along a common time axis. At a glance of the graph in FIG. 18, a correlation between peak of the per-minute exercise amount Wm, and lowest peak of the $SpO_2$ value can be clearly recognized. Specifically, in the graph of FIG. 18, there are recognized at least five exercise peak portions A, B, C, D, and E, which correspond to time zones when the per-minute exercise amounts Wm are excessively increased based on an assumption that the per-minute exercise amount Wm>40 is defined as a significant exercise. A first peak 491, a second peak 492, a third peak 493, a fourth peak 494, and a fifth peak 495 of the unit exercise amount estimation curve 49 overlap the exercise peak portions A, B, C, D, and E, respectively.

Observing the exercise peak portion A, a first lowest peak 481 of the $SpO_2$ curve 48 appears some time after the appearance of the first peak 491. Accordingly, the correlation between lowering of $SpO_2$ value and exercise can be clearly recognized. On the other hand, observing the exercise peak portion B, a part of the $SpO_2$ curve 48 corresponding to the second peak 492, which has a relatively low peak value, is a flat portion 482 where no significant lowering of $SpO_2$ value is recognized. Accordingly, it can be concluded that the $SpO_2$ value of the subject is not lowered by such a degree of exercise. Similarly to the exercise peak portion A, the third peak 493 of the unit exercise amount estimation curve 49 and the second lowest peak 483 of the $SpO_2$ curve 48 are correlated to each other regarding the exercise peak portion C, the fourth peak 494 of the unit exercise amount estimation curve 49 and the third lowest peak 484 of the $SpO_2$ curve 48 are correlated to each other regarding the exercise peak portion D, and the fifth peak 495 of the unit exercise amount estimation curve 49 and the fourth lowest peak 485 of the $SpO_2$ curve 48 are correlated to each other regarding the exercise peak portion E.

Also, a correlation between the exercise time Tw and/or the exercise amount sum Wa in the respective exercise peak portions A through E, and the first through the fourth lowest peaks 481, 483, 484, and 485 of the $SpO_2$ curve can be recognized in detail by detecting the exercise time Tw by the exercise time detector 332 based on the unit exercise amount estimation curve 49 shown in FIG. 18, and by obtaining the exercise amount sum Wa by implementing the mathematical formula (2) by the exercise amount sum calculator 333.

Figure 19:
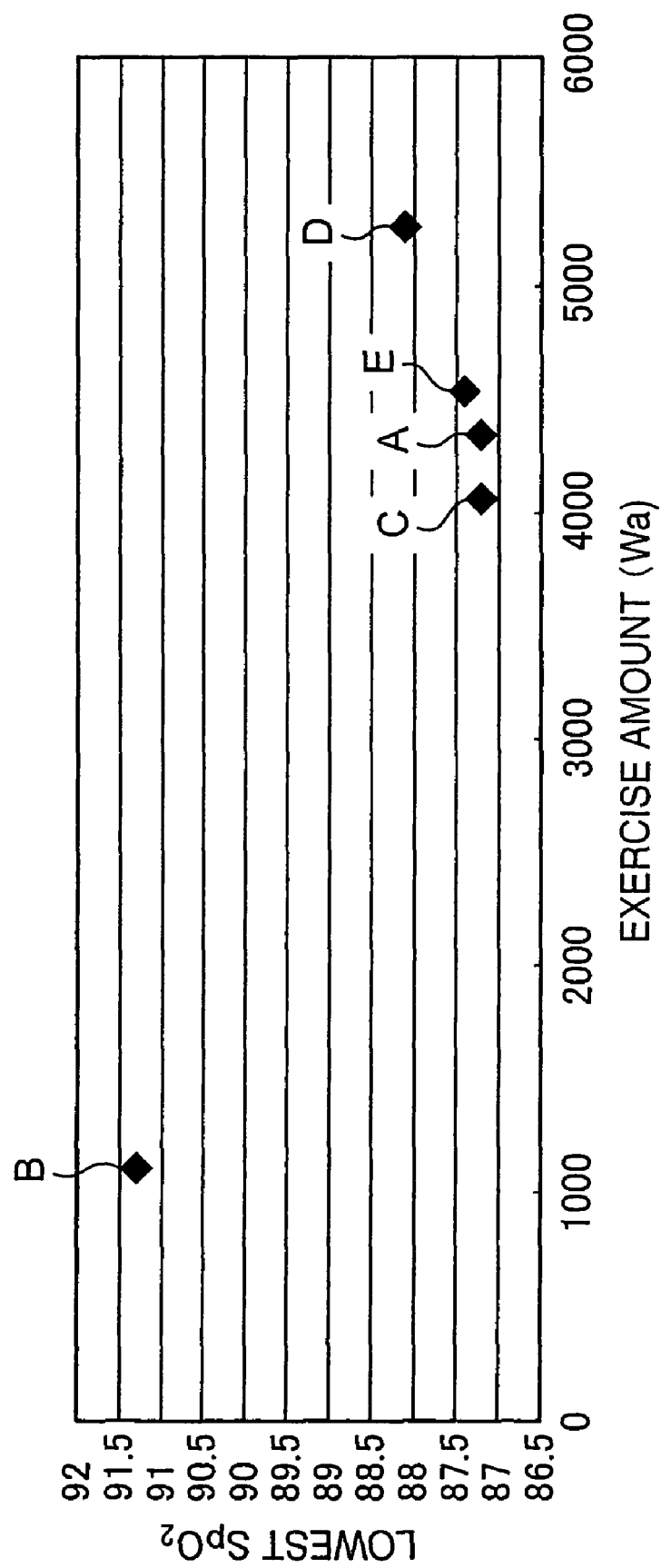
FIG. 19 is a graph, in which a relation between lowest $SpO_2$ value and exercise amount peak value is plotted in each of exercise peak portions A, B, C, D, and E in FIG. 18.

Specifically, the $SpO_2$ corresponding data generator 334 is operative to detect a lowest peak of the $SpO_2$ value, i.e., a lowest $SpO_2$ value in a time zone corresponding to the exercise time Tw in each of the exercise peak portions A through E, and to detect values of the first through the fifth peaks 491 through 495, i.e., exercise amount peak values in the respective exercise peak portions A through E, thereby enabling to clearly recognize a correlation between the lowest $SpO_2$ value and the exercise amount peak value. FIG. 19 is a graph, in which a relation between the lowest $SpO_2$ value and the exercise amount peak value is plotted in the respective exercise peak portions A through E. At a glance of the graph in FIG. 19, a correlation between the degree of the exercise done in the exercise time Tw, and lowering of $SpO_2$ value can be recognized.

Figure 20:
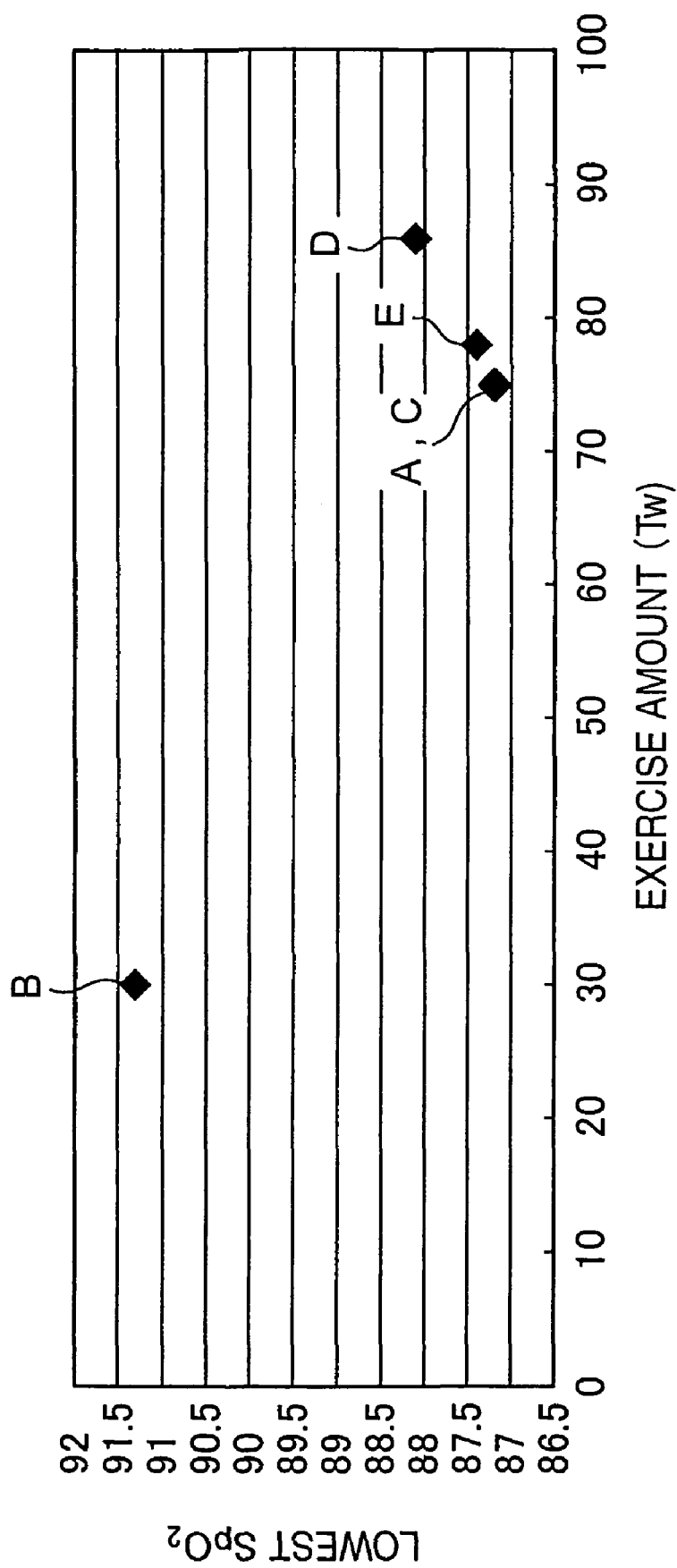
FIG. 20 is a graph, in which a relation between lowest $SpO_2$ value and exercise time Tw is plotted in each of the exercise peak portions A, B, C, D, and E in FIG. 18.

Also, the $SpO_2$ corresponding data generator 334 is operative to detect a lowest peak of the $SpO_2$ value, i.e., a lowest $SpO_2$ value in a time zone corresponding to the exercise time Tw in each of the exercise peak portions A through E, and to express the exercise time Tw in each of the exercise peak portions A through E in terms of numerical data, thereby enabling to clearly recognize a correlation between the lowest $SpO_2$ value and the exercise time Tw. FIG. 20 is a graph, in which a relation between the lowest $SpO_2$ value and the exercise time Tw is plotted in the respective exercise peak portions A through E. At a glance of the graph in FIG. 20, a correlation between the length of the exercise time Tw, and lowering of $SpO_2$ value can be recognized.

Returning to FIG. 8, the display controller 34 is a functioning part for displaying various data obtained by the $SpO_2$ data generator 31, the body motion data generator 32, and the exercise data generator 33 on the display unit 37 in the form of a certain image, and for outputting the various data to an output unit 38. The display controller 34 includes a data synthesizer 341 and a display data generator 342.

The data synthesizer 341 generates composite data, in which the body motion data and the $SpO_2$ data are expressed along a common time axis. Specifically, the data synthesizer 341 generates composite data, in which the $SpO_2$ curve generated by the $SpO_2$ data generator 31, and the actigraph generated by the actigraph creator 324 or the unit exercise amount estimation curve or the like generated by the exercise data generator 33 are expressed along the common time axis.

The display data generator 342 generates display/output data with use of the composite data generated by the data synthesizer 341. For instance, the display data generator 342 forms an image such as the graphs as shown in FIGS. 15 through 20, and displays the image on the display unit 37 or outputs the image to the output unit 38.

The oxygen flow rate calculator 35 calculates a proper oxygen flow rate to be supplied to the subject from an oxygen supplier such as a home oxygen therapy based on the correlation (see FIG. 19) between the lowest $SpO_2$ value generated by the $SpO_2$ corresponding data generator 334, and the exercise amount peak value. Specifically, the degree of exercise recommendable for the subject in his or her daily life can be recognized by obtaining the graph as shown in FIG. 19. Also, a correlation between the exercise and the lowering of the $SpO_2$ value can be recognized. Accordingly, a proper oxygen flow rate can be determined by creating an oxygen flow rate table showing a correlation between the lowest $SpO_2$ value and the exercise amount peak value, storing the oxygen flow rate table in the ROM 303 or a like device in advance, and by making a comparison between the calculation result of the $SpO_2$ corresponding data generator 334 and the oxygen flow rate table.

For instance, in the case where the result as shown in the graph of FIG. 19 is obtained for a subject, it is comprehended that the exercise amount in the range from 4,000 to 5,000 frequently appears in the daily life of the subject, and that the lowest $SpO_2$ value in association with the exercise amount is in the range from 88% to 87%. In this case, the proper oxygen flow rate from 1.3 to 1.5 litter/min. can be determined based on the table of FIG. 21. Accordingly, the oxygen flow rate calculator 35 calculates the proper oxygen flow rate of 1.3 to 1.5 litter/min. if the analysis result as shown in FIG. 19 is obtained, and proper oxygen flow rate information is displayed on the display unit 37 or outputted to the output unit 38.

(Description on Operation Flow)

Figure 22:
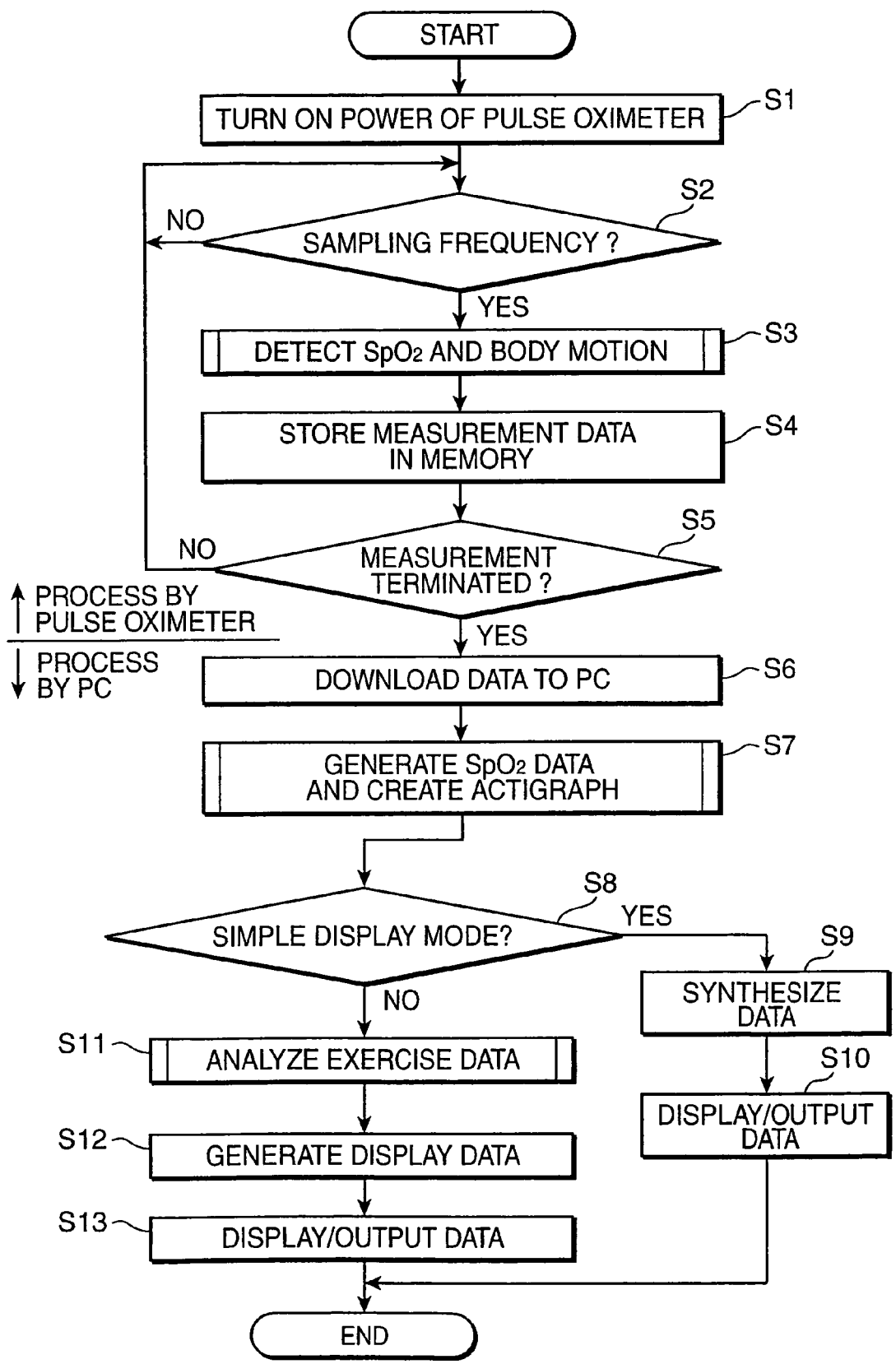
FIG. 22 is a flowchart showing an overall operation flow of the oximeter system shown in FIG. 3.

An operation of the oximeter system S having the above arrangement is described based on the flowcharts shown in FIGS. 22 through 27, and also referring to the block diagrams of FIGS. 7 and 8 according to needs. FIG. 22 is a flowchart showing a flow of overall operations of the oximeter system S. In this embodiment, a flow is described, in which the pulse oximeter 2 is attached to a subject H, as shown in FIG. 4, the $SpO_2$ value and the body motion of the subject H are concurrently detected for storage, the stored $SpO_2$ value and body motion of the subject H are read out from the pulse oximeter 2, and analysis data concerning a correlation between body motion and change of the $SpO_2$ value is obtained with respect to the subject H.

First, the pulse oximeter 2 is attached to the subject's body, and the power of the pulse oximeter 2 is turned on (Step S1). Specifically, the oximeter main body 200 is attached to an arm portion of the subject H with use of the fastening belt (not shown) serving as a fastening device, and a finger of the subject H is securely held by the probe 21 (see FIGS. 3 and 4). After completion of these operations, measurement is started. A timer may be set so that a time is started to be measured upon lapse of a certain time, considering a time required for the subject H to fall asleep in the case where an overnight pulse oximetry or the like is executed.

When the measurement is started, it is judged whether the current time is coincident with the time of the predetermined sampling frequency (Step S2). If it is judged that the current time is coincident with the time of the sampling frequency (YES in Step S2), measurement data concerning $SpO_2$ value or blood oxygen saturation information of the subject H is acquired from the probe 21, and measurement data concerning body motion information of the subject H is acquired from the three-axis acceleration sensor 22 (Step S3). Then, after A/D conversion or a predetermined computation is executed, the measurement data is stored in the memory 25 (see FIG. 7) of the pulse oximeter 2 (Step S4).

Then, it is judged whether the measurement is to be terminated (Step S5). In the case where it is judged that the system S is on halfway of the measurement (NO in Step S5), the routine returns to Step S2 to cyclically repeat the operations from Step S2 to Step S4. On the other hand, if the predetermined measurement period is ended, or the subject H intentionally terminates the measurement because he or she completely wakes up in the measurement period (YES in Step S5), the measurement operation with use of the pulse oximeter 2 is terminated.

Thereafter, as shown in FIG. 3, the pulse oximeter 2 and the PC 3 are connected by way of the USB cable 207 so that the measurement data stored in the pulse oximeter 2 is downloaded from the pulse oximeter 2 to the PC 3 (Step S6). Specifically, the measurement data concerning blood oxygen saturation information and body motion information, which is stored in the memory 25 of the pulse oximeter 2, is temporarily saved in the RAM 352 of the PC main body 30 via the oximeter I/F 27 and the PC I/F 351 (see FIG. 8).

Then, the measurement data downloaded to the PC 3 is analyzed by the $SpO_2$ data generator 31 and the body motion data generator 32 (Step S7). Specifically, the $SpO_2$ data generator 31 creates time-based data on the $SpO_2$ value, i.e., an $SpO_2$ curve by expressing count values corresponding to the $SpO_2$, which have been acquired in association with the data acquired time, along a time axis. Also, the body motion data generator 32 causes the actigraph creator 324 to create an actigraph representing the zero cross number in the form of a bar graph, for instance, after the filter processing and the zero cross counting, based on the count values corresponding to the time-based change of the body motion of the subject H in association with the data acquired time.

Subsequently, a mode of displaying the generated data, i.e., the degree of analyzation of the data on the display unit 37 is selected (Step S8). If a simple display mode of simply displaying the $SpO_2$ curve generated by the $SpO_2$ data generator 31 and the actigraph created by the actigraph creator 324 together on the display unit 37 is selected (YES in Step S8), the data synthesizer 341 of the display controller 34 expresses the $SpO_2$ curve and the actigraph on a common time axis (Step S9). Then, the display data generator 342 performs a certain data processing to display the composite data as a certain image, causes the display unit 37 to display the image such as the graph expressing the $SpO_2$ curve and the actigraph on the same time axis, e.g., the graphs as shown in FIGS. 13 through 15, or causes the output unit 38 to print out the image (Step S10).

If, on the other hand, the simple display mode is not selected in Step S8 (NO in Step S8), the respective parts in the exercise data generator 33 perform data presentation and data analysis in association with the exercise to allow the user to recognize a correlation between exercise and time-based change of $SpO_2$ value in detail (Step S11). The processing of Step S11 is described later in detail.

The data synthesizer 341 of the display controller 34 synthesizes the $SpO_2$ curve and the exercise-related analysis data generated by the exercise data generator 33, and the display data generator 342 of the display controller 34 converts the composite data into certain data for image formation (Step S12). For instance, the image such as the graphs as shown in FIGS. 16, 18 through 20 is displayed on the display unit 37 or outputted to the output unit 38 for printing (Step S13). Thus, the routine ends. This is the overall operation flow of the oximeter system S. Next, the flows of Steps S3, S7, and S11 are described in detail one by one.

Figure 23:
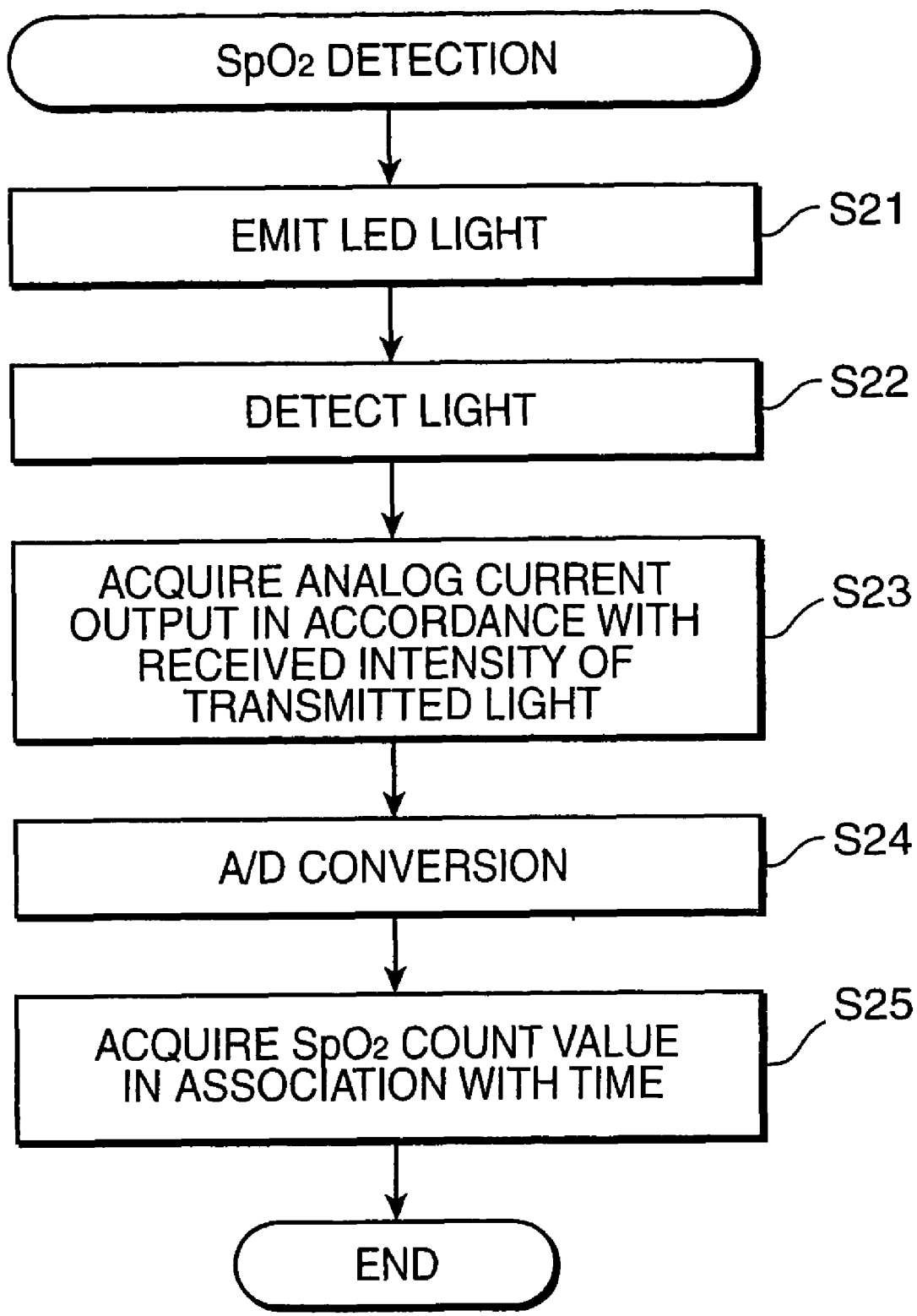
FIG. 23 is a flowchart showing details of $SpO_2$ detection in Step S3 of the flowchart of FIG. 22.

FIG. 23 is a flowchart showing details on the $SpO_2$ detection in Step S3 of the flowchart in FIG. 22. When it is judged that the current time is coincident with the time of the predetermined sampling frequency, the red LED 211R or the infrared 211IR (see FIG. 5) provided in the probe 21 are turned on to emit red light or infrared light toward the finger F of the subject H (Step S21). The light detector 212 detects transmitted light through the finger F in synchronization with the light emission (Step S22), and an analog current output in accordance with the received light intensity is acquired by the light detecting circuit 212C (Step S23).

The acquired analog current output is converted into a digital measurement signal by the first A/D converter 231 (see FIG. 7) (Step S24). Then, the $SpO_2$ count value detector 241 detects a count value of $SpO_2$ corresponding to the digital measurement signal at the predetermined sampling frequency (Step S25). The $SpO_2$ count value is stored in the measurement data storage 251 of the memory 25 in association with the time when the count value has been acquired. The above routine is cyclically repeated at the predetermined sampling frequency.

Figure 24:
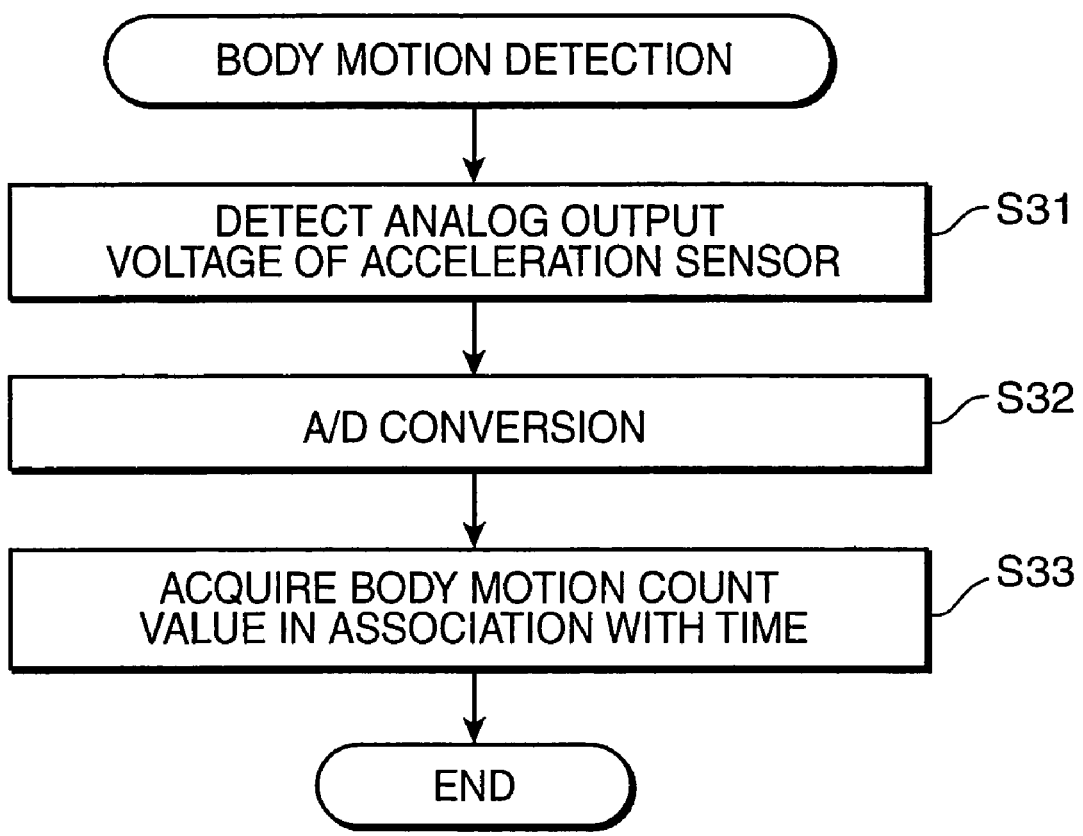
FIG. 24 is a flowchart showing details of body motion detection in Step S3 of the flowchart of FIG. 22

FIG. 24 is a flowchart showing details on the body motion detection in Step S3 of the flowchart in FIG. 22. When it is judged that the current time is coincident with the time of the sampling frequency, a sensor output, i.e., an analog current signal regarding one or all of the X-, Y-, and Z-axes of the three-axis acceleration sensor 22 (see FIG. 7) is obtained. The analog current signal is current-to-voltage converted into a voltage signal, which, in turn, is detected as an analog voltage signal with respect to the corresponding axis (Step S31).

The analog voltage signal is analog-to-digitally converted into a digital measurement signal by the second A/D converter 232 (Step S32). Then, the body motion count detector 242 detects a count value corresponding to one or all of the oscillations of the X-, Y-, and Z-axes, which correspond to the digital measurement signal obtained at the sampling frequency (Step S33). The count value corresponding to the one or all of the oscillations of the X-, Y, and Z-axes is stored in the measurement data storage 251 of the memory 25 in association with the time when the count value has been acquired. The above routine is cyclically repeated at the sampling frequency.

Figure 25:
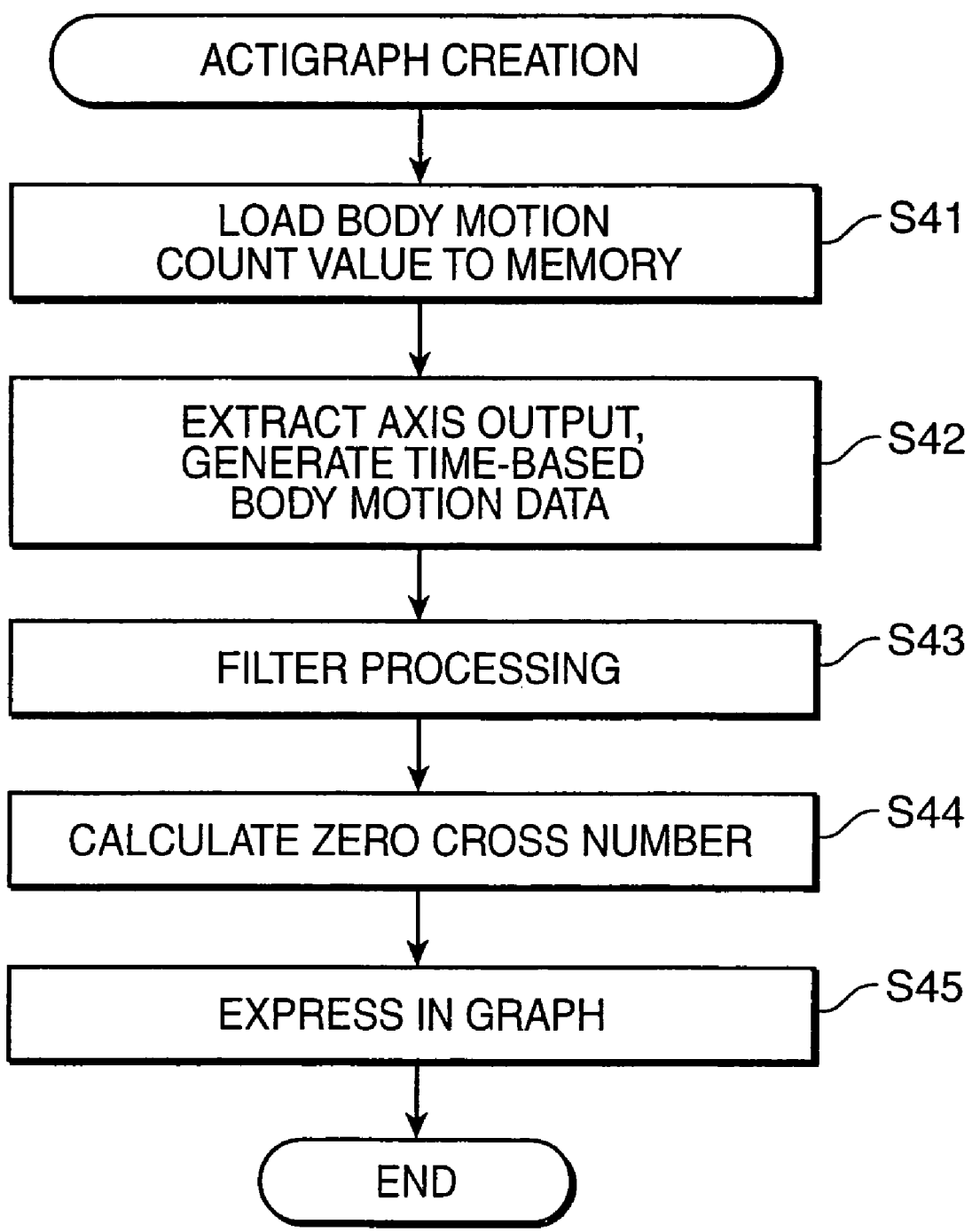
FIG. 25 is a flowchart showing details of actigraph creation in Step S7 of the flowchart of FIG. 22.

FIG. 25 is a flowchart showing details on the actigraph creation in Step S7 of the flowchart in FIG. 22. First, data concerning the count value corresponding to one or all of the oscillations of the X-, Y-, and Z-axes that has been downloaded from the oximeter 2 to the PC 3 is loaded to the RAM 352 or an equivalent device (Step S41). The data is data showing a time-based change of the body motion count value.

Then, the axis output detector 321 (see FIG. 8) extracts an output with respect to one of the X-, Y-, and Z-axes of the three-axis acceleration sensor 22, and the count value, i.e., an output voltage is expressed along a time axis, and data concerning the time-based change of the oscillation of the corresponding axis, namely, the body motion curve 41 concerning body motion of the subject H, is obtained (Step S42). Then, the filter processor 322 performs band-pass filter processing of extracting merely the signals in the range from about 2 to 3 Hz, which have a close relation to body motion (Step S43). The body motion curve after the filter processing is the body motion curve 42 as shown in FIG. 11, for example.

Subsequently, the zero cross number detector 323 counts the number of times when the body motion curve 42 crosses the zero level at the predetermined detection time interval T (=1 sec.) (Step S44, see FIG. 12). Then, the actigraph creator 324 creates data information, i.e., graph information such as the bar graphs as shown in FIGS. 13 through 15, for instance, with which the user can easily recognize the time-based change of the body motion or the exercise amount of the subject by expressing the zero-cross number information detected by the zero-cross number detector 323 along a time axis. Thus, the routine ends.

Figure 26:
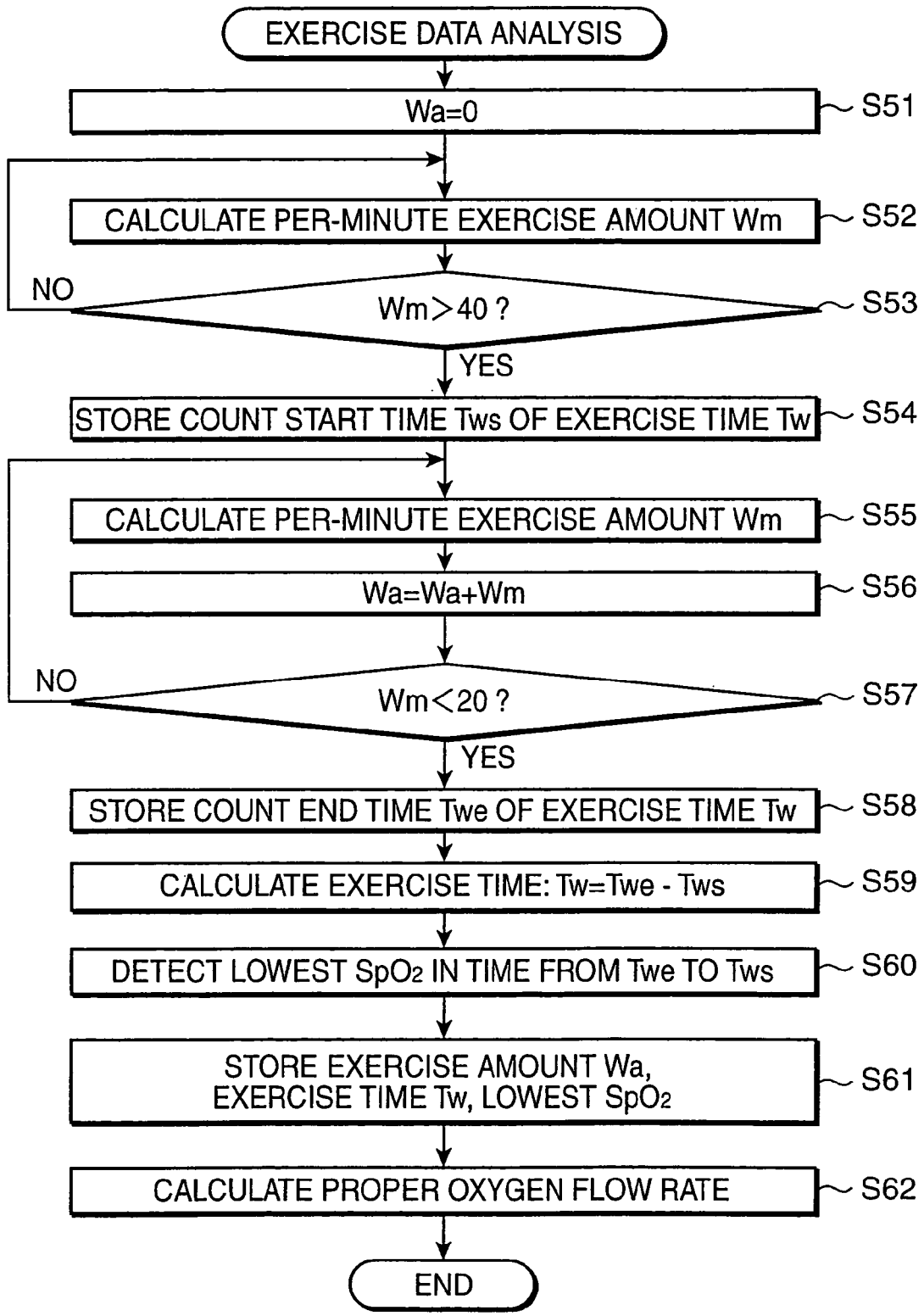
FIG. 26 is a flowchart showing details of exercise data processing in Step S11 of the flowchart of FIG. 22.

FIG. 26 is a flowchart showing details on the exercise data processing in Step S11 of the flowchart in FIG. 22. In FIG. 26, a computation flow of calculating the exercise time Tw and the exercise amount sum Wa based on the per-minute exercise amount Wm as described in the foregoing section is described. The flow is described on the assumption that Wm=40 at the exercise time count start point of time, and Wm=20 at the exercise time count end point of time.

First, a reset processing: Wa=0 is executed (Step S51). Then, the unit exercise amount calculator 331 calculates the per-minute exercise amount Wm based on the zero cross number, i.e., the per-second exercise amount Ws, which is detected by the zero cross number detector 323 at a time interval of 1 second (Step S52). Then, it is judged whether the obtained per-minute exercise amount Wm exceeds 40 counts (Step S53). If the per-minute exercise amount Wm is not larger than 40 counts (NO in Step S53), the routine returns to Step S52 without starting counting of the exercise time because the judgment result shows that a significant exercise of the subject H is not started. Then, the next per-minute exercise amount Wm is obtained by advancing the time along the time axis by the detection time interval T=1 sec.

If, on the other hand, it is judged that the per-minute exercise amount Wm exceeds 40 counts (YES in Step S53), the exercise time detector 332 starts counting the exercise time Tw. Since the counting is started, a count start point of time Tws of the exercise time Tw is stored in the RAM 302 or a like device (Step S54).

Subsequently, the per-minute exercise amount Wm is obtained by advancing the time along the time axis by one second (Step S55). Then, the exercise amount sum calculator 333 performs summation: Wa=Wa+Wm to obtain the exercise amount sum Wa (Step S56). The summation is continued until the per-minute exercise amount Wm is below 20 (NO in Step S57). Specifically, after the count start point of time Tws until the point of time when Wm<20, the summation of sequentially adding the per-minute exercise amount Wm so that the summation result becomes the exercise amount sum Wa is continued by sequentially advancing the time along the time axis by one second.

If, on the other hand, the per-minute exercise amount Wm is smaller than 20 counts (YES in Step S57), the exercise time detector 332 completes the counting of the exercise time Tw. The exercise amount sum Wa obtained in Step S56 immediately before the completion of the counting is set as the exercise amount sum Wa in the time zone corresponding to the exercise time Tw. Then, a count end point of time Twe of the exercise time Tw is stored in the RAM 302 or a like device (Step S58). Subsequently, the exercise time detector 332 calculates the exercise time Tw based on the following equation (Step S59).

$$Tw = Twe - Tws$$

where Tw represents the exercise time, Twe represents the count end point of time, and Tws represents the count start point of time.

Then, the $SpO_2$ corresponding data generator 334 detects a lowest peak of the $SpO_2$ value, i.e., a lowest $SpO_2$ value in the time zone from the count start point of time Tws to the count end point of time Twe (Step S60). Then, the exercise amount sum Wa obtained in Step S56, the exercise time Tw obtained in Step S59, and the lowest $SpO_2$ value obtained in Step S60 are stored in the RAM 302 or a like device (Step S61). Also, a proper oxygen flow rate to be supplied to the subject H is calculated by the oxygen flow rate calculator 35, according to needs, by making a comparison between the table as shown in FIG. 21, and the acquired exercise amount sum Wa and lowest $SpO_2$ value (Step S62). Thus, the routine ends.

Figure 27:
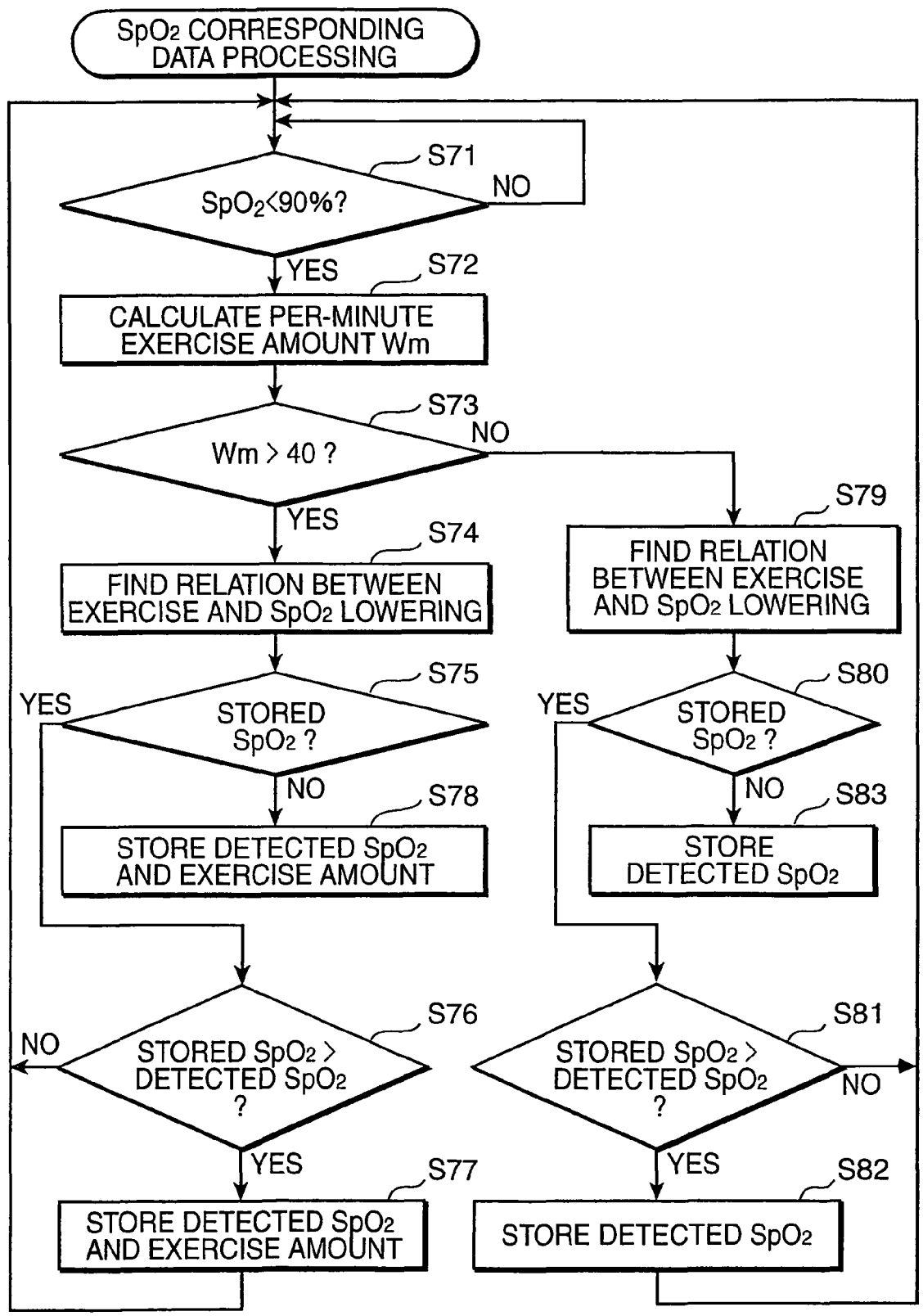
FIG. 27 is a flowchart showing a detection flow on lowest $SpO_2$ value, which is primarily executed by an $SpO_2$ corresponding data generator.

FIG. 27 is a flowchart showing a flow on lowest $SpO_2$ value detection, which is primarily executed by the $SpO_2$ corresponding data generator 334. Specifically, FIG. 27 is a process flow of detecting the lowest $SpO_2$ value while judging presence or absence of exercise. First, the $SpO_2$ values are successively extracted from the $SpO_2$ curve generated by the $SpO_2$ data generator 31 along the time axis, and it is judged whether the extracted $SpO_2$ value is lower than 90% (Step S71). If it is judged that the $SpO_2$ value is not lower than 90% (NO in Step S71), the next $SpO_2$ value is retrieved by advancing the time along the time axis by one second, which is cyclically repeated until the judgment result in Step S71 is affirmative.

If, on the other hand, the $SpO_2$ value is lower than 90% (YES in Step S71), it is judged whether the per-minute exercise amount Wm calculated by the unit exercise amount calculator 331 exceeds 40 counts (Step S73). Specifically, a judgment is made as to whether the lowering of $SpO_2$ value has a relevancy to the exercise. If Wm>40 (NO in Step S73), it is judged that the lowering of $SpO_2$ value has a relevancy to the exercise (Step S74).

Then, if it is judged that the lowest $SpO_2$ value has already been stored, namely, the stored $SpO_2$ value exists (YES in Step S75), a comparison is made between the stored $SpO_2$ value and the newly detected $SpO_2$ value (Step S76). If it is judged that the newly detected $SpO_2$ value is not larger than the stored $SpO_2$ value (YES in Step S76), the newly detected $SpO_2$ value and the exercise amount in association therewith are stored in the RAM 302 or a like device by data replacement (Step S77). If, on the other hand, the newly detected $SpO_2$ value is larger than the stored $SpO_2$ value (NO in Step S76), data replacement in the RAM 302 is not executed, and the routine returns to Step S71 to cyclically repeat the operation. If it is judged that there does not exist the stored $SpO_2$ value (NO in Step S75), the newly detected $SpO_2$ value and the exercise amount in association therewith are stored in the RAM 302 or a like device without data replacement (Step S78).

If, on the other hand, it is judged that the per-minute exercise amount Wm is smaller than 40 counts (NO in Step S73), it is judged that there is no correlation between the exercise and the lowering of $SpO_2$ value (Step S79). Similarly to the above operations, a judgment is made as to whether there has already been stored the lowest $SpO_2$ value, namely, there exists the stored $SpO_2$ value (Step S80). If the judgment result is affirmative (YES in Step S80), a comparison is made between the stored $SpO_2$ value and the newly detected $SpO_2$ value (Step S81). If it is judged that the newly detected $SpO_2$ value is not larger than the stored $SpO_2$ value (YES in Step S81), the newly detected $SpO_2$ value and the exercise amount in association therewith are stored in the RAM 302 or a like device by data replacement (Step S82). If, on the other hand, the newly detected $SpO_2$ value is larger than the stored $SpO_2$ value (NO in Step S81), data replacement in the RAM 302 is not executed, and the routine returns to Step S71 to cyclically repeat the operation. If it is judged that there does not exist the stored $SpO_2$ value (NO in Step S80), the newly detected $SpO_2$ value and the exercise amount in association therewith are stored in the RAM 302 or a like device without data replacement (Step S83).

(First Modification: Alert-Equipped Oximeter)

Figure 28:
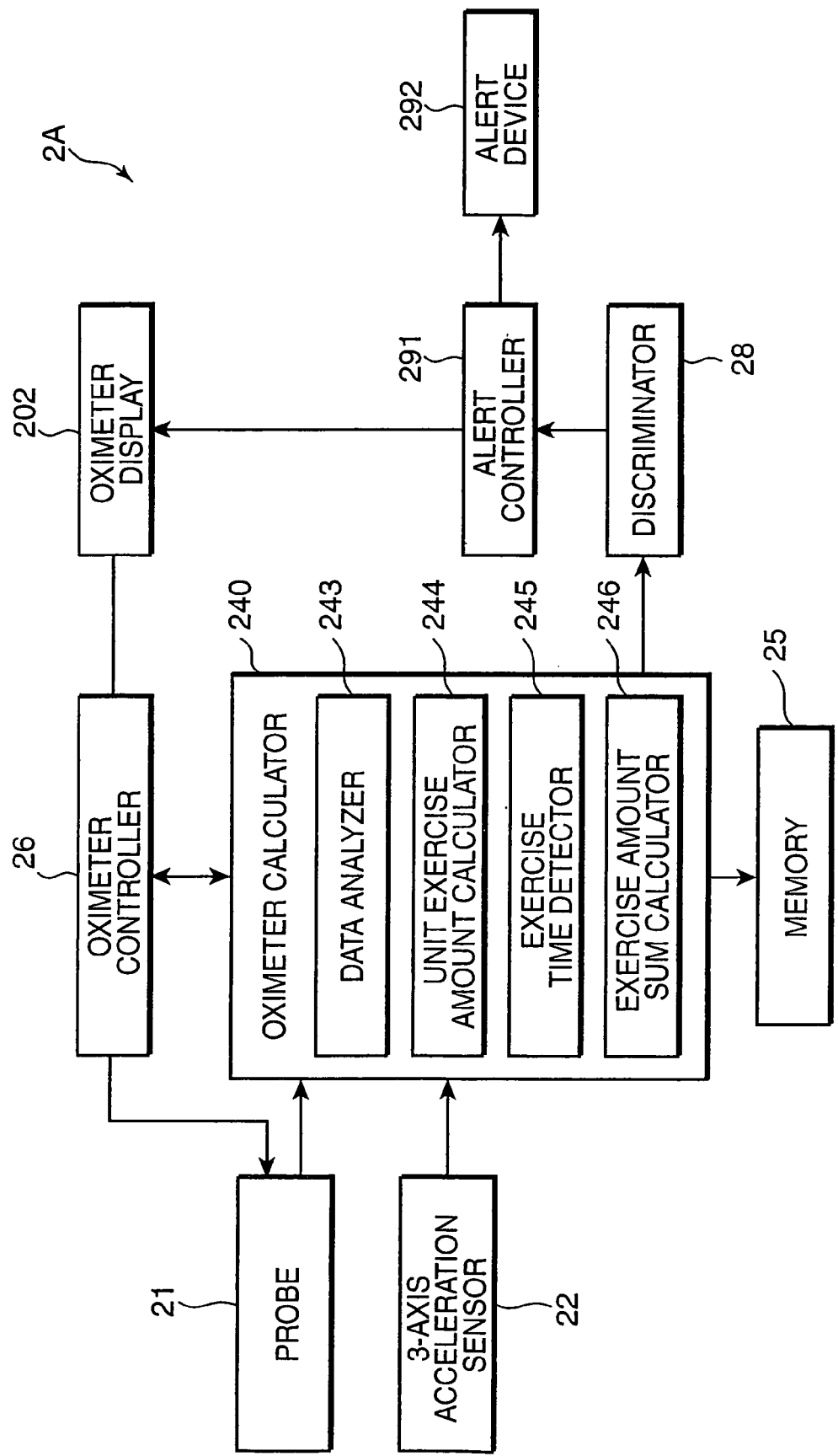
FIG. 28 is a block diagram showing an arrangement of an alert-equipped oximeter as a modified embodiment of the invention.

FIG. 28 is a block diagram showing an electrical configuration of an alert-equipped pulse oximeter 2A as a modified embodiment of the invention. The alert-equipped pulse oximeter 2A includes a probe 21, a three-axis acceleration sensor 22, a memory 25, an oximeter controller 26, and an oximeter display 202, as in the case of the pulse oximeter shown in FIG. 7, and also includes an oximeter calculator 240 having a function of analyzing exercise data, a discriminator 28, an alert controller 291, and an alert device 292. Description on the probe 21, the three-axis acceleration sensor 22, the memory 25, the oximeter controller 26, and the oximeter display 202 will be omitted herein.

The oximeter calculator 240 has a data analyzer 243, a unit exercise amount calculator 244, an exercise time detector 245, and an exercise amount sum calculator 246. The data analyzer 243 generates $SpO_2$ data and body motion data of a user based on body motion information detected by the three-axis acceleration sensor 22 and blood oxygen saturation information detected by the probe 21. Specifically, the data analyzer 243 has a function of the $SpO_2$ data generator 31 and the body motion data generator 32 described referring to FIG. 8. Also, the unit exercise amount calculator 244, the exercise time detector 245, and the exercise amount sum calculator 246 have functions similar to the unit exercise amount calculator 331, the exercise time detector 332, and the exercise amount sum calculator 333 provided in the exercise data generator 33 shown in FIG. 8, respectively.

The discriminator 28 discriminates whether a unit exercise amount, e.g., a per-minute exercise amount Wm calculated by the unit exercise amount calculator 244, and/or an exercise amount sum Wa calculated by the exercise amount sum calculator 246 exceeds a predetermined exercise amount threshold value. The exercise amount threshold value may be arbitrarily set depending on characteristics of the individual users such as the exercise limit of the user at which the $SpO_2$ value is lowered. Also, the discriminator 28 discriminates whether the $SpO_2$ value is lower than 90%.

The alert controller 291 causes the alert device 292 to issue an alert, or causes the oximeter display 202 to display an alert message depending on a discrimination result of the discriminator 28. Specifically, if the exercise amount of the user exceeds the predetermined exercise amount threshold value, or if the $SpO_2$ value of the user is lower than 90%, the alert controller 291 generates a control signal to issue an alert. The alert device 292 includes an alarm and a message recorder. The alert device 292 generates an alarm sound or an alert message in accordance with the control signal generated from the alert controller 291, and alerts the user of occurrence of abnormality.

Attaching the alert-equipped pulse oximeter 2A constantly to the user enables to cause the alert device 292 to issue an alert, or cause the oximeter display 202 to display an alert message if the user conducts an exercise which may induce lowering of the SpO$_2$ value, or if the SpO$_2$ value is actually lowered than 90%. This arrangement enables the user to readily recognize whether the user is in hazardous or abnormal condition.

(Second Modification: Oxygen Supply System)

Figure 29:
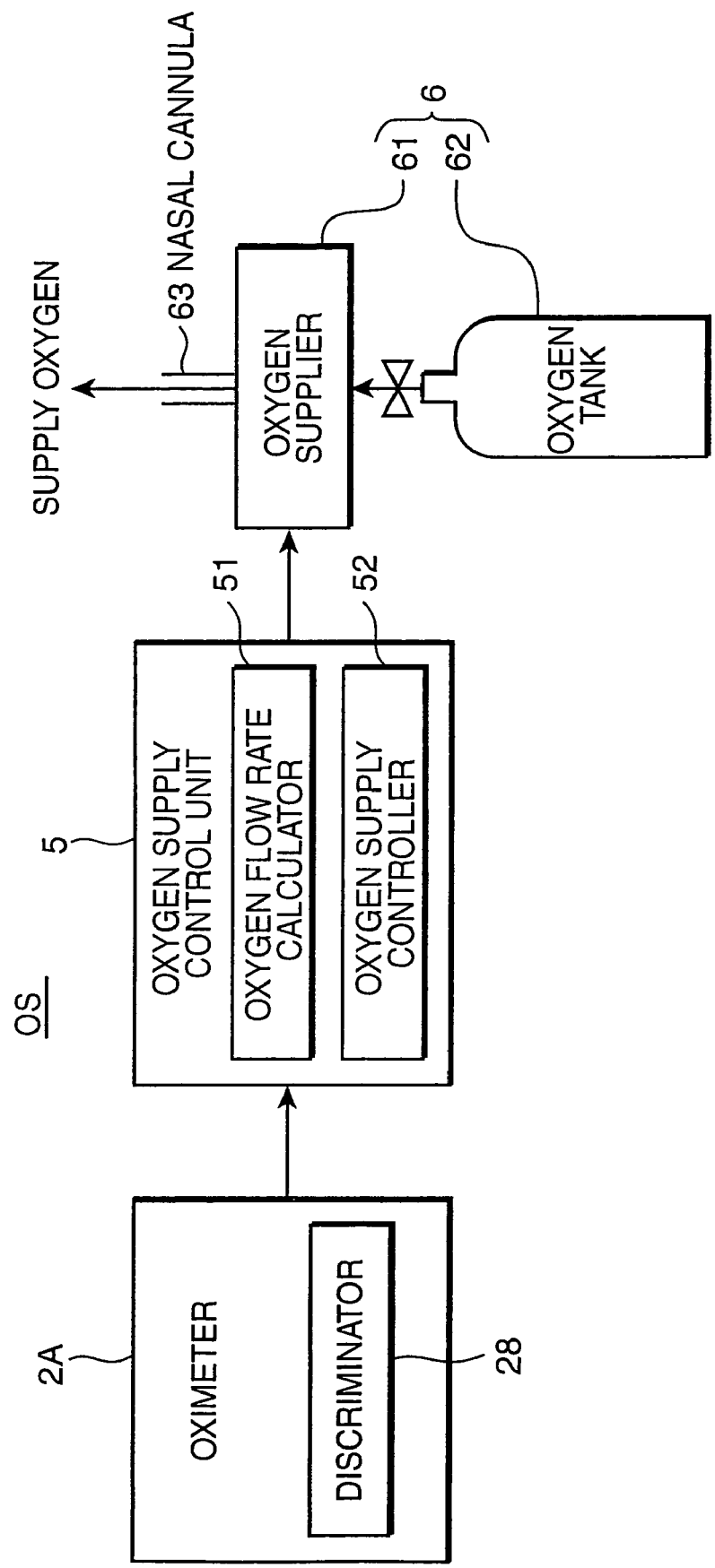
FIG. 29 is a block diagram showing an electrical configuration of an oxygen supply system as another modified embodiment of the invention.

FIG. 29 is a block diagram showing an electrical configuration of an oxygen supply system OS as another modified embodiment of the invention. The oxygen supply system OS includes the pulse oximeter 2A having the discriminator 28 shown in FIG. 28, an oxygen supply control unit 5, and an oxygen supply unit 6 having an oxygen supplier 61 and an oxygen tank 62. Similarly to the above modification, the discriminator 28 of the pulse oximeter 2A discriminates whether a per-minute exercise amount Wm and/or an exercise amount sum Wa exceeds a predetermined exercise amount threshold value, and also discriminates whether the SpO$_2$ value is lower than 90%.

The oxygen supply control unit 5 has an oxygen flow rate calculator 51 and an oxygen supply controller 52. The oxygen flow rate calculator 51 calculates a proper oxygen flow rate for the user depending on a discrimination signal issued from the discriminator 28. The oxygen flow rate calculator 51 is a functioning part for performing a similar calculation as the oxygen flow rate calculator 35 shown in FIG. 8, and has a table similar to the table as shown in FIG. 21 to calculate a proper oxygen flow rate required for the user by making a comparison between the table, and the exercise amount sum Wa and the lowest SpO$_2$ value detected by the pulse oximeter 2A.

The oxygen supply controller 52 generates a drive control signal and sends the control signal to the oxygen supplier 61 in supplying oxygen of the proper oxygen flow rate calculated by the oxygen flow rate calculator 51 to the user with use of the oxygen supplier 61. Upon receiving the control signal, the oxygen supplier 61 regulates the opening of a supply valve of the oxygen tank 62 to supply the oxygen to the user through a nasal cannula 63 or a like device. With the oxygen supply system OS, the proper oxygen flow rate can be determined by the oxygen supply control unit 5 in the case where the user who has to wear an oxygen mask including the nasal cannula 63 constantly, or on move, or in sleep conducts an exercise that may induce lowering of the SpO$_2$ value below a certain level. The arrangement enables to keep on supplying the oxygen to the user in such a manner that the lowering of the SpO$_2$ value can be eliminated with use of the oxygen supply unit 6.

(Third Modification: Operation Program Product of Oximeter System)

It is possible to provide an operation program product of executing a processing to be implemented by the oximeter system S, as another modified embodiment to carry out the invention. The program product may be provided by recording the program on a computer-readable recording medium, which is an attachment to a computer, such as a flexible disk, a CD-ROM, an ROM, an RAM, or a memory card. Also, the program product may be provided by recording the program on a recording medium equipped in the PC main body 30 shown in FIG. 3. Further alternatively, the program product may be provided by downloading via a network.

In general, the routines executed to implement the embodiment of the invention, whether implemented as part of an operating system or a specific application, component, program, object, module or sequence of instructions will be referred to as "programs". The program comprises one or more instructions that are resident at various times in various memory and storage devices in a computer, and that cause the computer to perform the steps necessary to execute steps or elements embodying the various aspects of the invention.

The embodiment of the invention has and will be described in the context of functioning the computer and computer system. However, those skilled in the art will appreciate that various embodiments of the invention are capable of being distributed as a program product in a variety of forms, and that the invention applies equally regardless of the particular type of signal bearing media used to actually carry out the distribution. Examples of signal bearing media include but are not limited to recordable type media such as volatile and non-volatile memory devices, floppy and other removable disks, hard disk drives, optical disks (e.g., CD-ROM's, DVD's, etc.), among others, and transmission type media such as digital and analog communication links, including the Internet.

As described above, a method for acquiring analysis data concerning a respiratory disease, comprises the steps of detecting a blood oxygen saturation and a body motion of a subject at a predetermined sampling frequency concurrently and respectively sequentially, expressing data concerning the detected blood oxygen saturation and data concerning the detected body motion along a common time axis, and acquiring analysis data concerning a relation between a change in the blood oxygen saturation and the body motion of the subject based on the blood oxygen saturation data and the body motion data expressed along the common time axis.

With this method, the serially detected data concerning the blood oxygen saturation and the body motion of the subject can be concurrently acquired. Accordingly, manual recording of behavior log can be eliminated. Since the acquired data serves as analysis data expressed along the common time axis, the user can accurately recognize the relation between the body motion and the change in the blood oxygen saturation of the subject.

According to the method, since the user can accurately recognize the relation between the body motion and the change in the blood oxygen saturation of the subject, the analysis data that enables to select a proper therapeutic apparatus and to prescribe a proper oxygen flow rate can be acquired.

An oximeter system comprises a blood oxygen saturation detector for detecting blood oxygen saturation information of a subject, a body motion detector for detecting body motion information of the subject, a controller for causing the blood oxygen saturation detector to acquire the blood oxygen saturation information, and causing the body motion detector to acquire the body motion information at a predetermined sampling frequency concurrently and respectively sequentially, and a display unit for displaying data concerning the acquired blood oxygen saturation information and data concerning the acquired body motion information along a common time axis.

With the above system, the blood oxygen saturation information detected by the blood oxygen saturation detector, and the body motion information detected by the body motion detector can be acquired at the predetermined sampling frequency concurrently and respectively sequentially. Accordingly, manual recording of behavior log can be eliminated. The blood oxygen saturation information data and the body motion information data can be displayed on the display unit along the common time axis.

According to the system, since the blood oxygen saturation information data and the body motion information data can be displayed on the display unit along the common time axis, observing the display image or the like on the display unit enables the user to easily and accurately recognize the relation between the body motion and the change in the blood oxygen saturation of the subject.

Another oximeter system comprises a blood oxygen saturation detector for detecting blood oxygen saturation information concerning a blood oxygen saturation of a subject, a body motion detector for detecting body motion information concerning a body motion of the subject, a controller for causing the blood oxygen saturation detector to acquire the blood oxygen saturation information, and causing the body motion detector to acquire the body motion information at a predetermined sampling frequency concurrently and respectively sequentially, an analyzer for analyzing a relation between a change in the blood oxygen saturation and the body motion of the subject based on data concerning the acquired blood oxygen saturation information and data concerning the acquired body motion information, and a display unit for displaying an analysis result by the analyzer.

With the above system, the blood oxygen saturation information detected by the blood oxygen saturation detector, and the body motion information detected by the body motion detector can be acquired at the predetermined sampling frequency concurrently and respectively sequentially. Also, the analyzer generates the analysis data concerning the relation between the change in the blood oxygen saturation and the body motion of the subject based on the blood oxygen saturation information data and the body motion information data, and the analysis result by the analyzer can be displayed on the display unit.

According to the system, not only the blood oxygen saturation information data and the body motion information data are displayed, but also the analysis result concerning the relation between the change in the blood oxygen saturation and the body motion of the subject are displayed. Accordingly, the user can easily acquire information necessary for diagnosing the respiratory disease in detail.

Preferably, the analyzer may be provided with a unit exercise amount calculator for sequentially calculating a unit exercise amount corresponding to a summation of the body motion information for a predetermined unit time based on the body motion information data, and a blood oxygen saturation data generator for generating time-based data of the blood oxygen saturation based on the blood oxygen saturation information data, and the display unit displays a relation between a time-based change of the unit exercise amount and a time-based change of the blood oxygen saturation.

With the above construction, the unit exercise amount is calculated as the summation of a detection value regarding the body motion information, which is detected by the body motion detector, e.g., every one second, for the predetermined unit time e.g. one minute. The body motion information of the subject can be acquired as objective data depending on the degree of body motion, i.e., a time-based change of the unit exercise amount by sequentially obtaining the unit exercise amount while sequentially advancing the time along the time axis by, e.g., one second from the point of time when the one-minute summation is started. Generally, a relation between body motion and change in blood oxygen saturation does not show instant responsiveness. A lowest peak of the blood oxygen saturation occurs some time after occurrence of a body motion. Accordingly, the user can accurately recognize whether a correlation between body motion, i.e., exercise, and change in the blood oxygen saturation is found in the subject by displaying a relation between the time-based change of the unit exercise amount, and the time-based change of the blood oxygen saturation.

According to the above system, the user can readily judge whether the subject has a characteristic that the blood oxygen saturation is likely to be lowered due to exercise, based on the relation between the time-based change of the unit exercise amount and the time-based change of the blood oxygen saturation displayed on the display unit. This arrangement enables to readily provide a therapeutic measure for the subject having a respiratory disease.

Preferably, the analyzer may be provided with an exercise time detector for detecting an exercise time when a significant exercise is presumed to have been conducted based on the unit exercise amount, referring to a predetermined reference value, and the display unit displays a relation between the exercise time and the time-based change of the blood oxygen saturation.

With the above construction, the user can accurately recognize whether a correlation between the length of the time when the significant exercise is presumed to have been conducted, and the time-based change of the blood oxygen saturation is found in the subject.

According to the above system, since the user can accurately recognize whether a correlation between the length of the time when the significant exercise is presumed to have been conducted, and the time-based change of the blood oxygen saturation is found in the subject, the characteristics of the individual subjects having a respiratory disease can be recognized in more detail.

It may be preferable that the analyzer includes an exercise amount sum calculator for calculating a sum of the unit exercise amount for the exercise time detected by the exercise time detector, and the display unit displays a relation between the sum of the exercise amount for the exercise time and the time-based change of the blood oxygen saturation.

With the above construction, the exercise time when the significant exercise is presumed to have been conducted, and the exercise amount done in the exercise time are quantized, and the relation between the length of the exercise time or the sum of the unit exercise amount, and the time-based change of the blood oxygen saturation is displayed on the display unit as the analysis result.

According to the above system, the relation between the exercise amount or the length of the exercise time, and the time-based change of the blood oxygen saturation can be recognized for each of the subjects in detail. Specifically, the user can recognize the relation between the degree of the exercise, and the time-based change of the blood oxygen saturation. This arrangement enables the user to determine a proper therapeutic measure for the individual subjects based on the analysis result, and to provide a concrete therapeutic measure such as the oxygen flow rate to be prescribed to the subject in need of oxygen supply.

The analyzer may be preferably provided with an oxygen flow rate calculator for calculating an oxygen flow rate required for the subject, based on a relation between the sum of the unit exercise amount calculated by the exercise amount sum calculator every interval of the exercise time, and the time-based change of the blood oxygen saturation.

With the above construction, the oxygen flow rate required for the subject can be automatically determined based on the relation between the sum of the unit exercise amount, and the time-based change of the blood oxygen saturation.

According to the above system, since the oxygen flow rate required for the subject can be automatically determined, diagnostic efficiency can be enhanced.

The analyzer may be preferably operative to set a threshold value for determining whether the body motion information is valid in extracting the body motion information from the body motion information data.

With the above construction, the body information reflecting the differences of the individual subjects can be acquired by setting the threshold value depending on the characteristics of the individual subjects. According to the system, an accurate analysis result reflecting the differences of the individual subjects can be obtained.

The body motion detector may be preferably provided with an acceleration sensor. With the above construction, the body motion information can be acquired as an axis output of the acceleration sensor. According to the above system, since the body motion information can be acquired as the axis output of the acceleration sensor, a simplified, compact, and light-weight system can be produced, and high reliability or high durability is ensured.

Preferably, the oximeter system may be further provided with a storage for storing the blood oxygen saturation information data and the body motion information data therein. In this case, the analyzer analyzes a relation between the change in the blood oxygen saturation and the body motion of the subject based on the blood oxygen saturation information data and the body motion information data stored in the storage.

Still another oximeter comprises a blood oxygen saturation detector for detecting blood oxygen saturation information concerning a blood oxygen saturation of a subject, a body motion detector for detecting body motion information concerning a body motion of the subject, a storage for storing data concerning the blood oxygen saturation information and data concerning the body motion information therein, and a controller for causing the blood oxygen saturation detector to detect the blood oxygen saturation information, and causing the body motion detector to detect the body motion information at a predetermined sampling frequency concurrently and respectively sequentially, and causing the storage to store the detected blood oxygen saturation information data and the detected body motion information data therein.

With the above constructions, the analysis data concerning the relation between the respiratory disease and the body motion of the subject can be acquired by attaching the pulse oximeter to the subject, detecting the blood oxygen saturation information and the body motion information, storing the blood oxygen saturation information data and the body motion information data in the memory, and reading the blood oxygen saturation information data and the body motion information data from the memory for analyzation by a processor such as a personal computer.

According to the above constructions, the subject performs overnight or 24-hour continuous oximetry at home by attaching the oximeter. After the oximetry, the data stored in the memory of the oximeter is analyzed in a medical institution or a like facility, and a correlation between the respiratory disease and the body motion of the subject is determined. In addition to the above advantages, manual recording of behavior log is eliminated. Accordingly, a load to the subject and the medical institution can be remarkably reduced.

The oximeter may be preferably provided with a unit exercise amount calculator for sequentially calculating a unit exercise amount corresponding to a summation of the body motion information for a predetermined unit time based on the body motion information data.

With the above construction, after the body motion information data of the subject is processed into objective data depending on the degree of body motion, i.e., the time-based change of the unit exercise amount, the processed objective data is stored in the memory of the oximeter, and read out from the memory for analyzation by the processor.

According to the above construction, since the data to be analyzed is stored in the memory of the oximeter as the time-based change of the unit exercise amount, the respiratory disease can be accurately diagnosed with use of a personal computer provided with a multi-purpose processor.

Preferably, the oximeter may be further provided with an exercise time detector for detecting an exercise time when a significant exercise is presumed to have been conducted based on the unit exercise amount, referring to a predetermined reference value, and an exercise amount sum calculator for calculating a sum of the unit exercise amount for the exercise time detected by the exercise time detector.

With the above construction, after the exercise time, the unit exercise amount, and the exercise amount sum are detected based on the body motion information data of the subject, the exercise time, the unit exercise amount, and the exercise amount sum are stored in the memory of the oximeter, and read out from the memory for analyzation by the processor.

According to the above construction, since the data to be analyzes is stored in the memory of the oximeter as the exercise time, the unit exercise amount, and the exercise amount sum, the respiratory disease can be accurately diagnosed with use of a personal computer provided with a multi-purpose processor.

Preferably, the oximeter may be further provided with a discriminator for discriminating whether the exercise unit amount or the sum of the unit exercise amount exceeds a predetermined threshold value, and an alert device for issuing an alert in response to a discrimination by the discriminator that the exercise unit amount or the sum of the unit exercise amount has exceeded the predetermined threshold value.

With the above construction, in the case where the subject conducts an exercise which may exceed the exercise amount threshold value set depending on the characteristics of the individual subjects, the alert device issues an alert. Accordingly, a proper measure of restraining the subject from conducting the exercise or the like is provided.

An oxygen supply system comprises an oximeter including a blood oxygen saturation detector for detecting blood oxygen saturation information concerning a blood oxygen saturation of a subject, a body motion detector for detecting body motion information concerning a body motion of the subject, a storage for storing data concerning the blood oxygen saturation information and data concerning the body motion information therein, a controller for causing the blood oxygen saturation detector to detect the blood oxygen saturation information, and causing the body motion detector to detect the body motion information at a predetermined sampling frequency concurrently and respectively sequentially, and causing the storage to store the detected blood oxygen saturation information data and the detected body motion information data therein, an exercise time detector for detecting an exercise time when a significant exercise is presumed to have been conducted based on the body motion information data, referring to a predetermined reference value, a unit exercise amount calculator for sequentially calculating a unit exercise amount corresponding to a summation of the body motion information for a predetermined unit time based on the body motion information data, and an exercise amount sum calculator for calculating a sum of the unit exercise amount for the exercise time detected by the exercise time detector, and an oxygen supply device including an oxygen supplier for supplying oxygen to the subject, a discriminator for discriminating whether the exercise unit amount or the sum of the unit exercise amount exceeds a predetermined threshold value, an oxygen flow rate calculator for calculating an oxygen flow rate required for the subject based on a relation between the unit exercise amount or the sum of the unit exercise amount, and a time-based change of the blood oxygen saturation, and an oxygen supply controller for causing the oxygen supplier to supply the oxygen in accordance with the oxygen flow rate calculated by the oxygen flow rate calculator if the discriminator discriminates that the exercise unit amount or the sum of the unit exercise amount has exceeded the predetermined threshold value.

With the above system, the oxygen flow rate required for the subject is calculated by the oxygen flow rate calculator based on the relation between the unit exercise amount or the exercise amount sum, and the time-based change of the blood oxygen saturation. The oxygen is supplied from the oxygen supplier in accordance with the oxygen flow rate calculated by the oxygen flow rate calculator.

According to the system, in the case where a patient in use of the oxygen supplier such as an oxygen tank constantly or on move, or in sleep conducts an exercise which may induce lowering of the blood oxygen saturation below a certain level, the oxygen can be supplied to the patient to eliminate the excessive lowered state of the blood oxygen saturation.

An operation program product for an oximeter system which is provided with a blood oxygen saturation detector for detecting blood oxygen saturation information concerning a blood oxygen saturation of a subject, a body motion detector for detecting body motion information concerning a body motion of the subject, a storage for storing data concerning the blood oxygen saturation information and data concerning the body motion information therein, and a processor, the operation program product allows a computer to execute the steps of causing the blood oxygen saturation detector to acquire blood oxygen saturation information of a subject and causing the body motion detector to acquire body motion information of the subject at a predetermined sampling frequency concurrently and respectively sequentially, causing the storage to store the detected blood oxygen saturation information data and the detected body motion information data therein, and acquiring the blood oxygen saturation information data and the body motion information data stored in the storage to analyze a relation between a change in the blood oxygen saturation and the body motion of the subject.

According to the operation program product, a computer system capable of accurately recognizing a relation between change in the blood oxygen saturation and body motion can be operated by analyzing the blood oxygen saturation information data and the body motion information data stored in the memory of the oximeter.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A method for acquiring analysis data concerning a respiratory disease, comprising the steps of:
   detecting a blood oxygen saturation and a body motion of a subject at a predetermined sampling frequency concurrently and respectively sequentially;
   expressing data concerning the detected blood oxygen saturation and data concerning the detected body motion along a common time axis;
   acquiring analysis data concerning a relation between a change in the blood oxygen saturation and the body motion of the subject based on the blood oxygen saturation data and the body motion data expressed along the common time axis; and
   calculating the subject's required oxygen flow rate based on a relation between a unit exercise amount or the sum of the unit exercise amount, and a time-based change of the blood oxygen saturation, with the unit exercise amount corresponding to a summation of the body motion information for a predetermined unit time based on the body motion data.

2. An oximeter system comprising:
   a blood oxygen saturation detector configured to detect blood oxygen saturation information concerning a blood oxygen saturation of a subject;
   a body motion detector configured to detect body motion information concerning a body motion of the subject;
   a controller configured to cause the blood oxygen saturation detector to acquire the blood oxygen saturation information, and cause the body motion detector to acquire the body motion information at a predetermined sampling frequency concurrently and respectively sequentially;
   an analyzer configured to analyze a relation between a change in the blood oxygen saturation and the body motion of the subject based on data concerning the acquired blood oxygen saturation information and data concerning the acquired body motion information; and
   a display unit configured to display an analysis result by the analyzer,
   wherein the analyzer includes:
   a unit exercise amount calculator configured to sequentially calculate a unit exercise amount corresponding to a summation of the body motion information for a predetermined unit time based on the body motion information data;
   a blood oxygen saturation data generator configured to generate time-based data of the blood oxygen saturation based on the blood oxygen saturation information data;
   an exercise time detector configured to detect an exercise time when a significant exercise is presumed to have been conducted based on the unit exercise amount, referring to a predetermined reference value;
   an exercise amount sum calculator configured to calculate a sum of the unit exercise amount for the exercise time detected by the exercise time detector; and
   an oxygen flow rate calculator configured to calculate the subject's required oxygen flow rate, based on a relation between the sum of the unit exercise amount calculated by the exercise amount sum calculator every interval of the exercise time, and the time-based change of the blood oxygen saturation, and the display unit displays:
      a relation between a time-based change of the unit exercise amount and a time-based change of the blood oxygen saturation;
      a relation between the sum of the exercise amount for the exercise time and the time-based change of the blood oxygen saturation; and
      a relation between the exercise time and the time-based change of the blood oxygen saturation.

3. The oximeter system according to claim 2, wherein the analyzer is operative to set a threshold value configured to determine whether the body motion information is valid in extracting the body motion information from the body motion information data.

4. The oximeter system according to claim 2, wherein the body motion detector includes an acceleration sensor.

5. The oximeter system according to claim 2, further comprising a storage configured to store the blood oxygen saturation information data and the body motion information data therein, wherein
the analyzer analyzes a relation between the change in the blood oxygen saturation and the body motion of the subject based on the blood oxygen saturation information data and the body motion information data stored in the storage.

6. An oximeter comprising:
a blood oxygen saturation detector configured to detect blood oxygen saturation information concerning a blood oxygen saturation of a subject;
a body motion detector configured to detect body motion information concerning a body motion of the subject:
a storage configured to store data concerning the blood oxygen saturation information and data concerning the body motion information therein;
a controller configured to cause the blood oxygen saturation detector to detect the blood oxygen saturation information, and cause the body motion detector to detect the body motion information at a predetermined sampling frequency concurrently and respectively sequentially, and cause the storage to store the detected blood oxygen saturation information data and the detected body motion information data therein;
a unit exercise amount calculator configured to sequentially calculate a unit exercise amount corresponding to a summation of the body motion information for a predetermined unit time based on the body motion information data;
an exercise time detector configured to detect an exercise time when a significant exercise is presumed to have been conducted based on the unit exercise amount, referring to a predetermined reference value;
an exercise amount sum calculator configured to calculate a sum of the unit exercise amount for the exercise time detected by the exercise time detector; and
an oxygen flow rate calculator configured to calculate the subject's required oxygen flow rate, based on a relation between the sum of the unit exercise amount calculated by the exercise amount sum calculator every interval of the exercise time, and the detected blood oxygen saturation information data.

7. The oximeter according to claim 6, further comprising:
a discriminator configured to discriminate whether the exercise unit amount or the sum of the unit exercise amount exceeds a predetermined threshold value; and
an alert device configured to issue an alert in response to a discrimination by the discriminator that the exercise unit amount or the sum of the unit exercise amount has exceeded the predetermined threshold value.

8. An oxygen supply system comprising:
an oximeter including:
a blood oxygen saturation detector configured to detect blood oxygen saturation information concerning a blood oxygen saturation of a subject;
a body motion detector configured to detect body motion information concerning a body motion of the subject:
a storage configured to store data concerning the blood oxygen saturation information and data concerning the body motion information therein;
a controller configured to cause the blood oxygen saturation detector to detect the blood oxygen saturation information, and cause the body motion detector to detect the body motion information at a predetermined sampling frequency concurrently and respectively sequentially, and cause the storage to store the detected blood oxygen saturation information data and the detected body motion information data therein;
an exercise time detector configured to detect an exercise time when a significant exercise is presumed to have been conducted based on a summation of the body motion information data, referring to a predetermined reference value;
a unit exercise amount calculator configured to sequentially calculate a unit exercise amount corresponding to a summation of the body motion information for a predetermined unit time based on the body motion information data; and
an exercise amount sum calculator configured to calculate a sum of the unit exercise amount for the exercise time detected by the exercise time detector, and
an oxygen supply device including:
an oxygen supplier configured to supply oxygen to the subject;
a discriminator configured to discriminate whether the exercise unit amount or the sum of the unit exercise amount exceeds a predetermined threshold value;
an oxygen flow rate calculator configured to calculate the subject's required oxygen flow rate based on a relation between the unit exercise amount or the sum of the unit exercise amount, and a time-based change of the blood oxygen saturation; and
an oxygen supply controller configured to cause the oxygen supplier to supply the oxygen in accordance with the oxygen flow rate calculated by the oxygen flow rate calculator if the discriminator discriminates that the exercise unit amount or the sum of the unit exercise amount has exceeded the predetermined threshold value.

9. A non-transitory operation program product for an oximeter system provided with a blood oxygen saturation detector configured to detect blood oxygen saturation information concerning a blood oxygen saturation of a subject, a body motion detector configured to detect body motion information concerning a body motion of the subject, a storage configured to store data concerning the blood oxygen saturation information and data concerning the body motion information therein, and a processor,
the operation program product allowing a computer to execute the steps of:
causing the blood oxygen saturation detector to acquire blood oxygen saturation information of a subject and causing the body motion detector to acquire body motion information of the subject at a predetermined sampling frequency concurrently and respectively sequentially;
causing the storage to store the detected blood oxygen saturation information data and the detected body motion information data therein;
acquiring the blood oxygen saturation information data and the body motion information data stored in the storage to analyze a relation between a change in the blood oxygen saturation and the body motion of the subject; and
calculating the subject's required oxygen flow rate based on a relation between a unit exercise amount or the sum of the unit exercise amount, and a time-based change of the blood oxygen saturation, with the unit exercise amount corresponding to a summation of the body motion information for a predetermined unit time based on the body motion data.

* * * * *